US007186545B2

(12) United States Patent
Collins et al.

(10) Patent No.: US 7,186,545 B2
(45) Date of Patent: Mar. 6, 2007

(54) **PROBIOTIC STRAINS FROM *LACTOBACILLUS SALIVARIUS* AND ANTIMICROBIAL AGENTS OBTAINED THEREFROM**

(75) Inventors: John Kevin Collins, Doughcloyne (IE); Gerald Christopher O'Sullivan, Bishopstown (IE); Gerardine Mary Thornton, Waterfall (IE); Marian Mary Geraldine O'Sullivan, Shankhill (IE)

(73) Assignees: Enterprise Ireland, Dublin (IE); University College Cork - National University of Ireland, Cork (IE)

( * ) Notice: Subject to any disclaimer, the term of this patent is extended or adjusted under 35 U.S.C. 154(b) by 283 days.

(21) Appl. No.: 10/606,114

(22) Filed: Jun. 26, 2003

(65) Prior Publication Data

US 2004/0214304 A1 Oct. 28, 2004

Related U.S. Application Data

(63) Continuation of application No. 09/367,105, filed as application No. PCT/IE98/00010 on Feb. 11, 1998, now abandoned.

(30) Foreign Application Priority Data

Feb. 11, 1997 (WO) .................. PCT/IE97/00007

(51) Int. Cl.
*C12N 1/20* (2006.01)
(52) U.S. Cl. .................. 435/252.9; 424/93.45
(58) Field of Classification Search .................. None
See application file for complete search history.

(56) References Cited

U.S. PATENT DOCUMENTS

| 4,347,240 A | 8/1982 | Mutai et al. |
| 5,032,399 A | 7/1991 | Gorbach et al. |
| 6,077,504 A | 6/2000 | Cavaliere ved. Vesley et al. |
| 6,132,710 A | 10/2000 | Panigrahi et al. |

FOREIGN PATENT DOCUMENTS

| EP | 1 384 319 A | 8/1990 |
| JP | 9-241173 A | 9/1997 |
| WO | WO 89/05849 A | 6/1989 |
| WO | WO 90/01335 A1 | 2/1990 |
| WO | WO 90/09398 A1 | 8/1990 |
| WO | WO 97/35596 A1 | 10/1997 |
| WO | WO 98/00035 A1 | 1/1998 |

OTHER PUBLICATIONS

T. R. Klaenhammer, FEMS Microbiology Reviews, 12 (1993) 39-86.
M. B. ten Brink et al., Journal of Applied Bacteriology 1994, 77 140-148.
Flynn et al., International Dairy Journal, (May-Jun. 1998) vol. 8, No. 5-6, pp. 581, Sep. 30-Oct. 2, 1997.
S. C. Jong et al., ATCC Quarterly Newsletter, vol. 13, No. 1, pp. 1-2 and 10-11, 1993.
TIBTECH, "Establishing a Scientific Basis for Probiotic R&D", vol. 12, pp. 6-8 (Jan. 1994).
Gilliland, FEMS Microbiology Reviews, vol. 87, pp. 175-188 (1990).
Adachi, The Lactic Acid Bacteria, vol. 1, "The Lactic Acid Bacteria in Health and Disease", pp. 233-261 (1992).
Marteau et al., FEMS Microbiology Reviews, vol. 12, pp. 207-220 (1993).
Kim, Cultured Dairy Products Journal, "Characterization of Lactobacilli and Bifidobacteria as Applied to Dietary Adjuncts", pp. 6-9 (Aug. 1988).
Fuller, Journal of Applied Bacteriology, vol. 66, pp. 365-378 (1989).
O'Sullivan et al., Trends in Food Science & Technology, vol. 31, pp. 309-314 (Dec. 1992).
Tannock, Human Intestinal Microflora in Health and Disease, pp. 517-539 (1983).
Lee et al., Trends in Food Science & Technology, vol. 6, pp. 241-245 (Jul. 1995).
Tancrede, Eur. J. Clin. Microbiol. Infect. Dis., vol. 11, pp. 1012-1015 (Nov. 1992).
Toba et al., Letters in Applied Microbiology, vol. 12, pp. 228-231 (1991).
K. Arihara et al., Lett. Appl. Microbiol. 1996, V22, p. 420-424.
Gardiner et al., Applied and Environment Microbiology, vol. 64, No. 6, pp. 2192-2199 (Jun. 1998).
J. K. Collins et al., Ini. Dairy Journal, vol. 8, pp. 487-490, (1998).
William P. Charteris et al., International Journal of Food Microbiology, vol. 35, pp. 1-27, (1997).
Seppo Salminen et al., International Journal of Food Microbiology, vol. 44, pp. 93-106, (1998).
C. Stanton et al., Int. Dairy Journal, vol. 8, pp. 491-496 (1998).
Collins et al., Demonstration of the Nutritional Functionality of Probiotic Foods FAIR-CT96-1028, Functional Food Research In Europe, 3rd Workshop, Haikko Manor, Finland, pp. 40-41 (Oct. 1-2, 1998).

(Continued)

Primary Examiner—Irene Marx
(74) Attorney, Agent, or Firm—Birch, Stewart, Kolasch & Birch, LLP

(57) ABSTRACT

A strain of *Lactobacillus salivarius* isolated from resected and washed human gastrointestinal tract inhibits a broad range of Gram positive and Gram negative microorganisms and secretes a product having antimicrobial activity into a cell-free supernatant. The activity is produced only by growing cells and is destroyed by proteinase K and pronase E, the inhibitory properties of the strain and its secretory products being maintained in the presence of physiological concentrations of human bile and human gastric juice. The strain exhibits a broad-spectrum of activity against bacteria including *Listeria, Staphylococcus*, including methocillin resistant *St. aureus* (MRSA), and *Bacillus*, but does not inhibit many closely related *lactobacilli*. An antimicrobial agent is obtained from the strain which has bacteriocin-like properties.

7 Claims, 10 Drawing Sheets

OTHER PUBLICATIONS

Morrisey et al., "Selection of a probiotic strain to modify human gut flora and a controlled trial of delivery and efficacy," *Irish Journal of Medical Science*, vol. 167, Supplement 8 (1998); Abstract from meeting of Irish Society for Gastroenterology, Jun. 12-13, 1998.

Sarem-Damerdji et al., *FEMS Microbiology Letters*, vol. 131, pp. 133-137 (1995).

O'Sullivan et al., The Human Gut as a Source of Probiotic Bacteria—Myth or Reality?, *Irish Journal of Medical Science*, vol. 162, Suppl. 11, p. 25, National Scientific Medical Meeting, Mar. 18-20, 1993.

Bouhnik, *Lait*, vol. 73, pp. 241-247, (1993) (Abstract provided).

Vaughan et al., *Journal of Applied Bacteriology*, vol. 76, pp. 118-123, (1994).

Prof. Kevin Collins, VTT Symposium 167, 1st Workshop, FAIR CT96-1028, Probdemo, Probiotic Lactobacilli—Towards Defining Selection and Functional Criteria, p. 27 (1996).

Collins et al., J. Roy Soc. Med International Congress and Symposium Series 219—Roy. Society of Medicine Press, 219:13-17 (1996).

Daly et al., "Biotechnology of lactic acid bacteria with special reference to bacteriophage resistance" (in Lactic Acid Bacteria: Genetics, Metabolism and Applications), Antonie van Leeuwenhoek, vol. 70, pp. 99-110 (1996).

Huis In't Veld et al., International Congress and Symposium Series 219, pp. 27-36, (1996).

Kawakami et al., *The Journal of Immunology*, vol. 132, No. 5, pp. 2578-2581 (May 1984).

Rowland, Toxicology of the Colon: Role of the Intestinal Microflora, In: Gibson G.R. (ed.) *Human Colonic bacteria: Role in nutrition, physiology and pathology*, 1995, pp. 155-172, Boca Raton CRC Press.

Legrand-Defretina et al., *LIPIDS*, vol. 26, No. 8, pp. 578-583, (1991).

Oksanen et al., *Annals of Medicine*, vol. 22, pp. 53-56, (1990).

Walker, "New Strategies for Mucosal Vaccination," *Vaccine*, vol. 12, pp. 387-400 (1994).

Isolauri et al., *Digestive Diseases and Sciences*, vol. 39, No. 12, pp. 2595-2600 (Dec. 1994).

Gibson, *Br. Journal of Nutrition*, vol. 80, Suppl. 2, pp. S209-S212 (1998).

Groot, *The Veterinary Quarterly*, vol. 20, Suppl. 3, pp. S45-S49, (Jun. 1998).

Kato et al., *Life Sciences*, vol. 63, No. 8, pp. 635-644, (1998).

Raychaudhuri et al., "Fully Mobilizing Host Defense: Building Better Vaccines," *Nat biotechnol.*, 16:1025-1031 (1998).

Steidler et al., *Infection and Immunity*, vol. 66, No. 7, pp. 3183-3189 (Jul. 1998).

McFarland et al., *Anaerobe*, vol. 3, pp. 73-78 (1997).

Henderson et al., (Cytokines, homeostasis, networks and disease) In: *Bacteria Cytokine Interactions In Health and Disease*, Portland Press, pp. 79-132 (1998).

Tagg et al., *Bacteriological Reviews*, vol. 40, No. 3, pp. 722-756 (Sep. 1976).

Collins et al., "Demonstration of probiotic function in a double blind placebo controlled clinical trials in adults," 3rd Workshop, Demonstration of the Nutritional Functionality of Probiotic Foods, FAIR-CT96-1028, Functional Food Research in Europe, Haikko Manor, Finland, pp. 40-41 (Oct. 1-2, 1998).

Siitonen et al., *Ann. Med.*, vol. 22, pp. 57-59 (1990).

Charteris et al., *Journal of Food Protection*, vol. 61, No. 12, pp. 1636-1643 (1998).

Dekker et al., *Chromatographia*, vol. 31, No. 11/12, pp. 549-553 (Jun. 1991).

O'Sullivan et al., "Isolation and selection of normal gut microflora for use as prophylactic probiotic agents," *Irish Journal of Medical Science*, Irish Society of Gastroenterology, p. 420 (Proceedings of meeting held in Dublin, Jun. 7 and 8, 1991).

Vaughan et al., *Journal of Applied Bacteriology*, vol. 73, pp. 299-308 (1992).

Savage, D.C., Interaction between host and its microbes. In: *Microbial Ecology of the Gut*, Clark and Bauchop (eds), Academic Press, London, pp. 277-310 (1977).

Charteris et al., *Journal Applied Microbiology*, vol. 84, pp. 759-768, (1998).

Mattila-Sandholm, VTT Symposium 173, Novel Methods for Probiotic Research, Technical Research Center of Finland, 2nd Workshop, FAIR CT96-1028, Probdemo, pp. 11-15, Espoo, Finland (1997).

Lucey et al., *Food Science and Technology Today*, vol. 11, No. 4, pp. 230-233, (1997).

Shanahan et al., "Grand Entry for Listeria," *Gastroenterology*, vol. 112, No. 3, pp. 1045-1046 (1997).

Thornton et al., "Determination of stringent criteria essential to the survival/growth/colonization of probiotic human intestinal tract bacteria," Book of Abstracts, European Commission Biotechnology and Fair Programmes, Conference on Lactic Acid Bacteria, Cork, Ireland (Oct. 22-26, 1995).

Collins, "Selection of Probiotic Strains and Potential Therapeutic Applications," Book of Abstracts, European Commission Biotechnology and Fair Programmes, Conference on Lactic Acid Bacteria, Cork, Ireland, p. 3 (Oct. 22-26, 1995).

Thornton et al., "The production of a novel anti-microbial substance by human intestinal microflora," *Irish Journal of Medical Science*, Supplement with Irish Society of Gastroenterology, Proceedings of Poster Section of Meeting held in Cork, pp. 603-604 (Jun. 3-4, 1994).

O'Sullivan et al., "Probiotic bacteria in the human gastro intestinal tract (Myth or Reality)," *Irish Journal of Medical Science*, Supplement with Proceedings with the Irish Society of Gastroenterology Meeting, Winter Meeting held Dec. 4-5, 1992 in Beaumont Hospital, Dublin.

Chauviere et al., *Journal of General Microbiology*, vol. 138, pp. 1689-1696 (1992).

Thornton et al., *Gasterentology*, vol. 108, No. 4, p. A928 (Apr. 1995).

O'Halloran et al., *International Dairy Journal*, vol. 8, No. 5/6, (published Oct. 16, 1998); Abstract from meeting held in Cork, Ireland Sep. 30-Oct. 2, 1997.

Flynn et al., *International Dairy Journal*, vol. 8, No. 5/6, (published Oct. 16, 1998); Abstract from meeting held in Cork, Ireland Sep. 30-Oct. 2, 1997.

Gardiner et al., *International Dairy Journal*, vol. 8, No. 5/6, p. 597 (published Oct. 16, 1998); Abstract from meeting held in Cork, Ireland Sep. 30-Oct. 2, 1997.

Murphy et al., *International Dairy Journal*, vol. 8, No. 5/6, (published Oct. 16, 1998); Abstract from meeting held in Cork, Ireland Sep. 30-Oct. 2, 1997.

Thornton et al., "Human intestinal probiotic bacteria: Production of anti-microbial factors," *Irish Journal of Medical Science*, Supplement with Proceedings of the Irish Society of Gastroenterology, pp. 362-363, Proceedings of Meeting Held in Craigavon on May 28-29 (1993).

Thornton et al., "Bile acid tolerance and deconjugating activity of lactobility," *Irish Journal of Medical Science*, Supplement with Proceedings of the Irish Society of Gastroenterology, Proceedings of Winter Meeting, Dublin, Nov. 25-26, 1994, p. 578.

PROBIOTIC STRAINS FROM *LACTOBACILLUS SALIVARIUS* AND ANTIMICROBIAL AGENTS OBTAINED THEREFROM

This application is a continuation of application Ser. No. 09/367,105, filed on Nov. 10, 1999, now abandoned, and for which priority is claimed under 35 U.S.C. § 120, application Ser. No. 09/367,105 is the national phase of PCT International Application No. PCT/IE98/00010 filed on Feb. 11, 1998, under 35 U.S.C. § 371. The entire contents of each of the above-identified applications are hereby incorporated by reference. This application also claims priority of International Application No. PCT/IE97/00007 filed on Feb. 11, 1997, under 35 U.S.C. § 119.

FIELD OF THE INVENTION

This invention relates to probiotic bacterial strains capable of producing antimicrobial agents which have various applications in food stuffs and in medicine. More particularly, the invention relates to probiotic strains of *Lactobacillus salivarius* and to a peptide antibacterial agent derived therefrom with bacteriocin-like properties.

BACKGROUND ART

Much research has been carried out in the field of human probiotics in the last decade (see review Huis in't Veld et al. (1994) *Tibtech* 12, 6–8). This research has been prompted by the rising interest by the public in their health and well-being. Many probiotic products are now available on the market and some of the beneficial effects derived from these products range from alleviation of lactose intolerance (Gilliland, S. E. (1990) *FEMS Microbiol. Rev.* 87, 175–188) to prevention of diarrheal diseases (Marteau, P. et al. (1993) *FEMS Microbiol. Rev.* 12, 207–220) and possible prevention of carcinogenesis (Adachi, S. (1992) In "The Lactic Acid Bacteria in Health and Disease". (Wood, Ed.), 233–262, Elsevier, Barking). Controversy exists over many of these beneficial effects as no standardised procedures are available and contradictory results have been published with regard to the possible beneficial effects of cultured products containing 'probiotic' bacteria.

Poor choice of strain has been cited as one of the contributing factors to the inconsistency and variability of results (Marteau, P. et al. (1993) supra) (Kim, H. S. (1988) Cult. Dairy Prod. J. 23, 6–9) and Fuller, R. ((1989) *J. Appl. Bact.* 66, 365–378) outlined criteria pertaining to the successful isolation of probiotic strains. The strains should be indigenous to the intended host species and also have the ability to (i) survive and grow within that host; (ii) exert a beneficial effect at the target site and (iii) be maintainable in the carrier food or system throughout product manufacture and storage.

There is a fast growing market for health-promoting products including probiotics. Many such products are now available (Jong, S. C. and Birmingham, J. M., (1993) *ATCC Quart. Newslett.* 13(1), 1–11). One of the more important components of these products is the microorganisms used. The most frequently utilised species include *Bifidobacterium* sp., *Lactobacillus* sp., and *Propionibacterium* sp. (O'Sullivan, M. G., et al. (1992) *Trends in Food Sci. and Tech.* 3(12), 309–314). There is a lack of substantiated evidence from controlled trials that the organisms currently used in such products are those which have beneficial effects on the gut flora (Tannock, G. W. (1983) *In Human Intestinal Microflora in Health and Disease* 517–5399 D. J. Hentges (ed.), New York, Academic Press). The source of the microorganism is critical to its survival and therefore its function in the human intestinal tract. Lee, Y-K and Salminen, S. ((1995) *Trends Food Sci. Technol.* 6, 241–245) stated that as a general requirement, a probiotic strain should be of human origin as some health-promoting effects may be species dependent. It is well known that the indigenous microflora is one of the major defense mechanisms that protects the human against colonisation by allochthonous invading bacteria (Tancrede, C. (1992) *Eur. J. Clin. Microbiol. Infect. Dis.* 11(11), 1012–1015) and it is also the human's best ally when supporting the immune system. Bacterial populations at different levels of the gastrointestinal tract constitute complex ecosystems depending on the physiology of the host and on interactions between bacteria.

Ten Brink et al. ((1994) Journal of Applied Bacteriology 77 140–148) isolated and screened a large number (~1000) of *Lactobacillus* strains for the production of antimicrobial activity. *Lactobacilli* were isolated from various fermented foods and feeds (sauerkraut, cheese, sausage and silage), human dental plaque and faeces derived from different laboratory animals (rat, mouse, guinea pig and quail) and human volunteers. Only eight positive strains were found and two of these were studied, namely *Lactobacillus salivarius* M7 and *Lactobacillus acidophilus* M46. The former strain produces the broad spectrum bacteriocin salivaricin B which inhibits the growth of *Listeria monocytogenes, Bacillus cereus, Brochothrix thermosphacta, Enterococcus faecalis* and many *lactobacilli*. *L. acidophilus* M46 produces a bacteriocin acidocin B which combines the inhibition of *Clostridium sporogenes* with a very narrow activity spectrum within the genus *Lactobacillus*. However, these strains are not indigenous to the infected host species, which is one of the criteria which is required for a successful probiotic strain for human use.

Arihara, K. et al. ((1996) Letters in Applied Microbiology 22, 420–424) have isolated Salivacin 140 a bacteriocin from *Lactobacillus salivarius* subsp. *salicinius* T140. Strain T140 was isolated from the surface of Japanese pampas grass leaves grown close to an animal barn and thus the strain was likely to have derived from animal faeces.

There is a need for probiotic strains which meet the aforementioned criteria. Bacteriocin production by *lactobacilli* is thought to play an important role in the competitive exclusion of pathogens and other undesirable microorganisms of the intestinal tract of humans. Bacteriocins are broadly defined as proteinaceous compounds which exhibit a bactericidal effect against a wide range of microorganisms.

Due to their diversity of species and habitats *lactobacilli* are the most bacteriocinogenic of the lactic acid bacteria. As many as forty bacteriocins produced by *lactobacilli* have now been isolated (Klaenhammer, T. R. (1993) *FEMS Microbiol. Rev.* 12, 39–86).

Bacteriocins have been isolated from human infant faeces. However, the bacteriocins were found to have narrow host ranges and were active only against other lactobacillus species (Toba, T. et al. (1991) *Lett. Appl. Microbiol.* 12, 228–231.).

There is a need for bacteriocins with a broad spectrum of activity.

DISCLOSURE OF INVENTION

The invention provides a strain of *Lactobacillus salivarius* isolated from resected and washed human gastrointestinal tract which inhibits a broad range of Gram positive and Gram negative microorganisms and which secretes a product having antimicrobial activity into a cell-free supernatant, said activity being produced only by growing cells and being destroyed by proteinase K and pronase E, the inhibitory properties of said strain and its secretory products being maintained in the presence of physiological concentrations of human bile and human gastric juice.

Preferably, the strain of *Lactobacillus* according to the invention exhibits a broad-spectrum of activity against bacteria including *Listeria*, *Staphylococcus* and *Bacillus*, but does not inhibit many closely related *lactobacilli*.

Two especially preferred strains are *Lactobacillus salivarius* strain UCC 1 (deposited at The National Collections of Industrial and Marine Bacteria Limited (NCIMB) on Nov. 27, 1996, and accorded the accession number NCIMB 40830) and *Lactobacillus salivarius* strain UCC 118 (deposited at NCIMB on Nov. 27, 1996, and accorded the accession number NCIMB 40829) and mutants or variants thereof having the same properties.

The antimicrobial product secreted by the *Lactobacillus salivarius* strains according to the invention may be the expression product of a plasmid or other extrachromosomal entity associated with said strains.

The invention also provides a health promoting product containing a strain of *Lactobacillus salivarius* as hereinbefore defined as a probiotic.

The strains of *Lactobacillus salivarius* according to the invention were isolated from appendices and sections of the large and small intestine of the human gastrointestinal tract (G.I.T.) obtained during reconstructive surgery.

A preferred site for the isolation of the strains according to the invention is the small intestine. Any bacteria which prove difficult to maintain in culture were discarded as they would not be suitable to work with under processing or manufacturing conditions.

In this way certain strains of *Lactobacillus salivarius* were identified which have a greater chance of survival in the human G.I.T. when compared to many of the probiotic strains currently being used.

The strains according to the invention when subjected to adhesion assays are found to be highly adherent to both Caco-2 and HT-29 cell-lines.

The strains of *lactobacilli* according to the invention are able to survive at pH as low as 2.0. Prior to colonisation and growth of a probiotic in the gastrointestinal tract it must pass through the harsh acidic environment of the stomach. There are four main factors which determine the survival of bacteria on passage through the stomach to reach the intestine, namely the pH of the gastric juice, the buffering capacity of food, the rate of gastric emptying and the quantity and physiological state of the bacterium itself.

Gastric acid has been implicated as a major host defence mechanism involved in maintaining the sparse bacterial population of the upper small bowel and aiding resistance against infection by pathogenic microorganisms (germicidal activity). A key factor influencing survival of bacteria in gastric juice is pH.

The mechanism of tolerance of a probiotic strain to low pH is of importance for its ability to survive passage through the stomach. Prolonged incubation of the cells of the *lactobacillus* strains according to the invention in buffered media prior to challenge at low pH values show that they are sensitive to pH 2.0. This observation indicates that these strains possess an inducible acid tolerance mechanism for resistance as hereinafter exemplified.

The *lactobacillus* strains according to the invention also exhibit high bile resistance. It is considered that resistance to bile acids is an important biological strain characteristic required for survival in the hostile environment of the G.I.T. For microorganisms to have a health-promoting capacity in the human intestine not only must they be able to resist the potentially lethal effects of the bile acids present but they must not impinge on the health of the host by producing toxic compounds such as deoxycholic acid (DCA) and lithocholic acid (LCA) which have been implicated in a number of cytotoxic phenomena.

The invention also provides an antimicrobial agent obtained from a strain of *Lactobacillus salivarius* according to the invention as hereinbefore defined which has bacteriocin-like properties.

Preferably, the antimicrobial agent according to the invention has the following properties:
(i) An apparent molecular weight between 30 and 100 kDa;
(ii) Heat stability;
(iii) Resistance over a wide pH range;
(iv) Resistance to treatment with detergents;
(v) Resistance to organic solvents;
(vi) Sensitivity to proteolytic enzymes including proteinase K, pronase E, trypsin, α-chymotrypsin, ficin and papain; and
(vii) Resistance to lipase, catalase, alkaline phosphatase, phospholipase C and lipoprotein lipase.

Two of the *Lactobacillus salivarius* strains according to the invention, namely *L. salivarius* strains UCC 1 and UCC 118 were screened for antimicrobial activity against a set of four indicator strains, *Listeria innocua*, *Pseudomonas fluorescens*, *Escherichia coli* and *Lactobacillus fermentum* KLD. These strains when tested on buffered medium were found to be inhibitory towards *Listeria innocua* and *L. fermentum* KLD indicator strains. Inhibition studies demonstrated that the two strains inhibited a broad range of Gram positive and Gram negative microorganisms. Both strains secreted antimicrobial activity into the cell-free supernatant and this activity was destroyed by proteinase K and pronase E. Therefore, these compounds were considered to be bacteriocins.

The *L. salivarius* strains UCC 1 and UCC 118 produce secretory proteinaceous compounds which have been given the code names ABP1 and ABP118, respectively.

ABP1 and ABP118 exhibit quite a broad-spectrum of activity against bacteria including *Listeria*, *Staphylococcus* and *Bacillus* but do not inhibit closely related *lactobacilli*, with the exception of *L. fermentum* KLD, or other LAB such as *Leuconostoc*, *Streptococcus* or *Bifidobacterium*. This is an unusual trait of a bacteriocin (Klaenhammer, T. R. (1993) supra). and is likely to be advantageous for the use of these strains as probiotics since they would compete against undesirable microorganisms but not against closely related strains. Another unusual feature of the strains is their antagonistic activity towards *Pseudomonas* sp. This is an unusual trait for Gram positive bacteria.

UCC strains 1 and 118 have a much broader spectrum of activity than their respective proteinaceous compounds, ABP1 and ABP118. This would suggest that the viable cells produce a product which either enhances or acts in synergy with ABP1/ABP118 to inhibit the target cell.

ABP1 and ABP118 are not identical bacteriocins (they possess different spectra of inhibition) but are very similar, as both are not active against LAB and each producer is immune to the activity of the other's bacteriocin. Cross immunity may indicate that these bacteriocins act in the same manner. ABP118 is active against some methicillin resistant *S. aureus* (MRSA), *H. pylori* and *P. fluorescens* strains. No reports exist to date in the literature of inhibition of MRSA by a bacteriocin.

The invention also provides a purified fraction of an antimicrobial agent hereinbefore identified as ABP118 and which has the following properties:

(i) A molecular weight of 5.0–5.3 kDa;
(ii) A relative amino acid composition which has greater than 45% of hydrophobic amino acids, 19–21% glycine, 13–14% alanine and 11–12% leucine, no tryptophan or tyrosine, one methionine and four proline residues;
(iii) An amino acid sequence -Lys-Arg-Gly-Pro-Asn-C (SEQ ID NO: 1) at or adjacent to the N-terminus; and
(iv) Comprises an amino acid sequence Asn Met Lys Arg Gly Pro Asn Cys Val Gly Asn Phe Leu Gly Gly Leu Phe Ala Gly Ala Ala Ala Gly Val Pro Gln Gly Pro Cys (SEQ ID NO: 2).

The antimicrobial agent ABP118 has an unusually broad spectrum of activity as hereinafter described and exemplified.

The invention also provides a purified fraction of an antimicrobial agent hereinbefore identified as ABP1 and which has the following properties:

(i) A molecular weight of 5.3–6.1 kDa; and
(ii) A relative amino acid composition which has greater than 28–30% of hydrophobic amino acids, 17% glycine and 12–13% alanine, no tryptophan and two proline residues.

As indicated above, *Lactobacillus salivarius* strain UCC 118, isolated from human intestine, produces the antibacterial protein, ABP118 which exhibits a broad range of inhibition towards Gram positive and some Gram negative bacteria. ABP118 has been shown to be heat stable, resistant over a wide pH range and resistant to treatment with a number of detergents and organic solvents. It is sensitive to proteolytic enzymes and insensitive to lipase activity. Ultrafiltration suggests an apparent molecular weight between 30- and 100-kDa for a crude extract of ABP118. Growth studies demonstrate that maximum production of ABP118 occurs in MRS broth pH 5.5. Removal of either Tween 80 (Trade Mark) or peptones from this medium results in 50% loss in ABP118 production. *L. salivarius* UCC 118 produces ABP118 in milk-based media and in the presence of physiological concentrations of human bile (0.3% (v/v)). Co-culturing experiments demonstrate the ability of *L. salivarius* UCC 118 to inhibit growth of *Salmonella* in a broth medium. It is considered that this is due to the production of antimicrobial compounds including ABP118.

The bacteriocin ABP118 can be detected in an active and available form in the presence of milk proteins. Thus, milk can be used as a support medium for bacteriocin production in accordance with the invention. Furthermore, the strains of *Lactobacillus salivarius* according to the invention can be used for fermenting milk products.

The above mentioned properties of ABP118, namely pH, temperature and storage stability mean that this bacteriocin is likely to be of value in the food and pharmaceutical industries.

Thus, the antimicrobial agent according to the invention can be used in foodstuffs. It can also be used as a medicament.

The antimicrobial agent according to the invention is particularly useful against methicillin resistant *S. aureus* (MRSA).

As hereinafter demonstrated in Examples 7 and 8, the above amino acid sequence (SEQ ID NO: 2), which was determined from a purified fraction of the bacteriocin, is a partial peptide. This partial peptide was used to design probes which identified an internal gene sequence and from this sequence an 80 bp fragment was isolated and sequenced. This DNA sequence was deduced to give a protein sequence which confirms the identity of SEQ ID NO: 2. Thus, the invention provides a DNA sequence coding for the bacteriocin ABP118, namely the DNA sequence 5'ATGAAACGCGGACCC AACTGTGTAGGTAACT-TCTTAGGTGGTCTATTTGCTGGAGCA GCTGCAGGT-GTCCCCCAGGGCCC3'(SEQ ID NO: 6).

Figure 1:
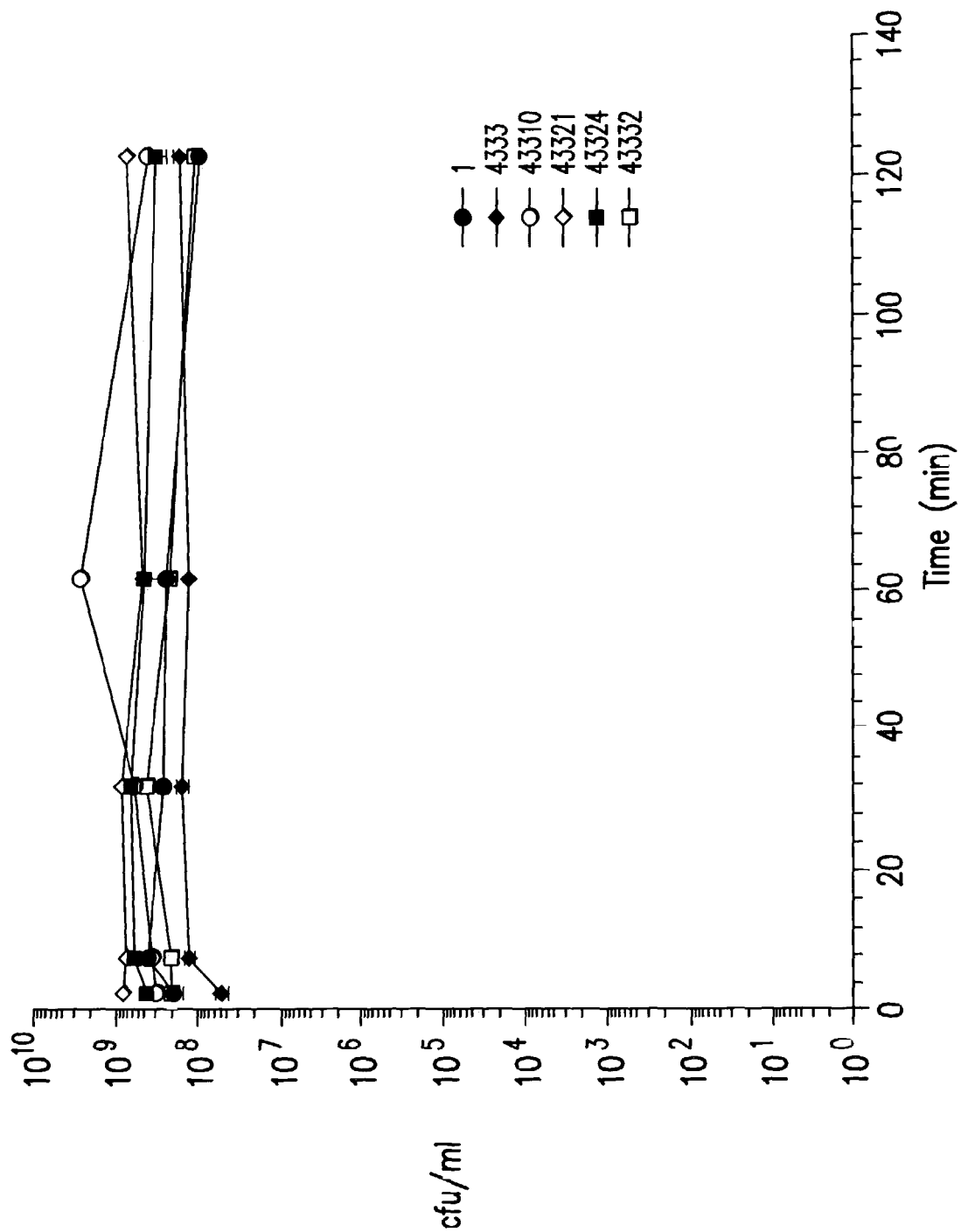
FIG. 1 is a graphic representation of the survival of washed cells of *Lactobacillus* strains (cfu/ml) in MRS broth, pH 2.0 versus time (min)

The invention will be further illustrated by the following Examples.

MODES FOR CARRYING OUT THE INVENTION

EXAMPLE 1

Isolation of Probiotic Bacteria

Appendices and sections of the large-and small intestine of the human G.I.T., obtained during reconstructive surgery, were screened for probiotic bacterial strains as shown in Table 1.

TABLE 1

Gastrointestinal tract tissue samples screened for the presence of probiotic bacteria

| Sample | Location |
| --- | --- |
| A | Ileum |
| B | Colon |
| C | Ileal-caecal region |
| D | Appendix |

TABLE 1-continued

Gastrointestinal tract tissue samples screened for the presence of probiotic bacteria

| Sample | Location |
|---|---|
| E | Appendix |
| F | Ileum |
| G | Ileal-caecal region |

All samples were stored immediately after surgery at −80° C. in sterile containers.

Frozen tissues were thawed, weighed and placed in cysteinated (0.05%) one quarter strength Ringers' solution. Each sample was gently shaken to remove loosely adhering microorganisms (termed—wash 'W'). Following transfer to a second volume of Ringers' solution, the sample was vortexed for 7 min to remove tightly adhering bacteria (termed—sample 'S'). In order to isolate tissue embedded bacteria, samples A, B and C were also homogenised in a Braun blender (termed—homogenate 'H'). The solutions were serially diluted (dilution $10^{-1}$ from a wash sample was labelled W1, dilution $10^{-2}$ was labelled W2 and the same labelling system was used for the 'S' and 'H' samples) and spread-plated (100 µl) on to the following agar media: RCM (reinforced clostridial media) and RCM adjusted to pH 5.5 using acetic acid; TPY (trypticase, peptone and yeast extract), Chevalier, P. et al. (1990) *J. Appl. Bacteriol* 68, 619–624). MRS (deMann, Rogosa and Sharpe); ROG (acetate medium (SL) of Rogosa); LLA (liver-lactose agar of Lapiere); BHI (brain heart infusion agar); LBS (*Lactobacillus* selective agar) and TSAYE (tryptone soya agar supplemented with 0.6% yeast extract). All agar media was supplied by Oxoid Chemicals with the exception of TPY agar. Plates were incubated in anaerobic jars (BBL, Oxoid) using $CO_2$ generating kits (Anaerocult A, Merck) for 2–5 days at 37° C.

Gram positive, catalase negative rod-shaped or bifurcated/pleomorphic bacteria isolates were streaked for purity on to complex non-selective media (MRS and TPY). Isolates were routinely cultivated in MRS or TPY medium unless otherwise stated at 37° C. under anaerobic conditions. Presumptive *Lactobacillus* sp. were stocked in 40% glycerol and stored at −20° and −80° C.

Fermentation End-product Analysis

Metabolism of the carbohydrate glucose and the subsequent organic acid end-products were examined using an LKB Bromma, Aminex HPX-87H High Performance Liquid Chromatography (HPLC) column. The column was maintained at 60° C. with a flow rate of 0.6 ml/min (constant pressure). The HPLC buffer used was 0.01 N $H_2SO_4$. Prior to analysis, the column was calibrated using 10 mM citrate, 10 mM glucose, 20 mM lactate and 10 mM acetate as standards. Cultures were propagated in modified MRS broth for 1–2 days at 37° C. anaerobically. Following centrifugation for 10 mm at 14,000 g, the supernatant was diluted 1:5 with HPLC buffer and 200 µl was analysed in the HPLC. All supernatants were analysed in duplicate.

Biochemical and Physiological Characterisation

Biochemical and physiological traits of the bacterial isolates were determined to aid identification. Nitrate reduction, indole formation and expression of β-galactosidase activity were assayed. Growth at both 15° C. and 45° C., growth in the presence of increasing concentrations of NaCl up to 5.0% and protease activity on gelatin were determined. Growth characteristics of the strains in litmus milk were also assessed.

Species Identification

The API 50CHL (BioMerieux SA, France) system was used to tentatively identify the *Lactobacillus* species by their carbohydrate fermentation profiles. Overnight MRS cultures were harvested by centrifugation and resuspended in the suspension medium provided with the kit. API strips were inoculated and analysed (after 24 and 48 h) according to the manufacturers' instructions. Identity of the *Lactobacillus* sp. was confirmed by SDS-Polyacrylamide gel electrophoresis analysis (SDS-PAGE) of total cell protein.

Enzyme Activity Profiles

The API ZYM system (BioMericux, France) was used for semi-quantitative measurement of constitutive enzymes produced by the *Lactobacillus* isolates. Bacterial cells from the late logarithmic growth phase were harvested by centrifugation at 14,000 g for 10 min. The pelleted cells were washed and resuspended in 50 mM phosphate buffer, pH 6.8 to the same optical density. The strips were inoculated in accordance with the manufacturers' instructions, incubated for 4 h at 37° C. and colour development recorded.

Antibiotic Sensitivity Profiles

Antibiotic sensitivity profiles of the isolates were determined using the 'disc susceptibility' assay. Cultures were grown up in the appropriate broth medium for 24–48 h, spread-plated (100 µl) onto agar media and discs containing known concentrations of the antibiotics were placed onto the agar. Strains were examined for antibiotic sensitivity after 1–2 days incubation at 37° under anaerobic conditions. Strains were considered sensitive if zones of inhibition of 1 mm or greater were seen.

Plasmid Profile Analysis

Plasmid profile analysis of ten *Lactobacillus* sp. was performed using the (Anderson, D. L. and McKay L. L., (1983) *Appl. Env. Microbiol.* 46, 549–552) lysis procedure with the following modifications. Bacterial cells were inoculated (4%) into 100 ml MRS broth supplemented with 40 mM DL-threonine and incubated for 4–5 h (mid-log phase). Cells, harvested by centrifugation, were used immediately for the plasmid DNA preparation. Before the lysis step, lysozyme (10 mg/ml) and mutanolysin (10 µg/ml) were added to the cell suspensions and incubated at 37° C. for 1 h and subsequently at 4° C. for 30 min. After the addition of 5 M NaCl, the lysates were put on ice for 30 min. The DNA was electrophoresed on 0.7% vertical agarose gels in Tris-acetate buffer for 4–5 h at 100V.

Isolation of *Lactobacillus* sp.

Seven tissue sections taken from the human G.I.T. were screened for the presence of strains belonging to the *Lactobacillus* genus. There was some variation between tissue samples as follows. Samples A (ileum) and E (appendix) had the lowest counts with approximately $10^2$ cells isolated per gram of tissue. In comparison, greater than $10^3$ cfu/g tissue were recovered from the other samples. Similar numbers of bacteria were isolated during the 'wash' and 'sample' steps with slightly higher counts in the 'sample' solutions of F (ileum) and G (ileal-caecal). Of those screened for tightly-adhering bacteria (homogenised), C (ileal-caecal) was the only tissue section that gave significant counts.

During the screening of some tissue sections, for example C and B, there was not a direct correlation between counts obtained during a dilution series. This would indicate that some growth factors, either blood or tissue derived, were being provided for the growth of the fastidious bacteria in the initial suspension which was subsequently diluted out.

Strain Selection and Characterisation

Approximately fifteen hundred catalase negative bacterial isolates from different samples were chosen and characterised in terms of their Gram reaction, cell size and morphology, growth at 15° and 45° C. and fermentation end-products from glucose. Greater than sixty percent of the isolates tested were Gram positive, homofermentative cocci arranged either in tetrads, chains or bunches. Eighteen percent of the isolates were Gram negative rods and heterofermentative *coccobacilli*. The remaining isolates (twenty-two percent) were predominantly homofermentative *coccobacilli*. Thirty eight strains were characterised in more detail—13 isolates from G; 4 from F; 8 from D; 9 from C; 3 from B and 1 from E. All thirty eight isolates tested negative both for nitrate reduction and production of indole from tryptophan.

Species Identification

The API 50CHL allowed rapid identification of the *Lactobacillus* isolates.

Seven of the isolates were very typical of the *salivarius* species according to their carbohydrate fermentation profiles. All seven fermented fructose, glucose, mannose, sorbose and raffinose efficiently. None fermented amygdaline. There was some variability: four of the strains fermented ribose, two were negative for lactose utilisation and three isolates partially fermented rhamnose. These, however, are not uncommon traits of the *salivarius* sp. (Bergey's Manual). Three of the isolates possessed similiar fermentation profiles to *Lactobacillus casei* subsp. *casei*. They fermented ribose, galactose, glucose, fructose, arbutine, cellobiose, lactose, saccharose, tagatose and gluconate. However, none fermented gentibiose or turanose and one strain was negative for growth on sorbitol and amygdaline. The three isolates fermented glycerol which is a trait common to twenty percent of *casei* subsp. *casei* strains. Five isolates were tentatively classified in the *plantarum/pentosus* group. They were positive for fermentation of ribose, galactose, glucose, fructose, sorbitol, lactose, cellibiose and esculine. All but two fermented melezitose, four were positive for trehalose, two were positive for tagatose and one for gluconate. All fermented L-arabinose but only one fermented D-arabinose. None were able to grow on raffinose. Analysis of total cell protein of the *Lactobacillus* sp. by SDS-PAGE revealed two main species, *salivarius* and *paracasei*.

A summary of the strain identification is included in Table 2. In Table 2 and in the following Tables 3–6 and the related description the prefix UCC has been omitted for the *Lactobacillus* strains.

TABLE 2

Identification of selected *Lactobacillus* strains by two different techniques

| Strain | Sugar fermentation profiles | Total cell protein (SDS-PAGE)* |
|---|---|---|
| *Lactobacillus* sp. | | |
| 1 | *L. salivarius* | *L. salivarius* subsp. *salivarius* |
| 4333 | *L. salivarius* | *L. salivarius* subsp. *salivarius* |
| 43310 | *L. salivarius* | *L. salivarius* subsp. *salivarius* |
| 43321 | *L. salivarius* | *L. salivarius* subsp. *salivarius* |
| 43324 | *L. salivarius* | *L. salivarius* subsp. *salivarius* |
| 43332 | *L. casei* subsp. *casei* | *L. paracasei* subsp. *paracasei* |

TABLE 2-continued

Identification of selected *Lactobacillus* strains by two different techniques

| Strain | Sugar fermentation profiles | Total cell protein (SDS-PAGE)* |
|---|---|---|
| 43336 | *L. casei* subsp. *casei* | ND |
| 43338 | *L. plantarum* | *L. paracasei* subsp. *paracasei* |
| 43348 | *L. pentosus* | *L. salivarius* subsp. *salivarius* |
| 43361 | ND | *L. salivarius* subsp. *salivarius* |
| 43362 | *L. plantarum* | *L. paracasei* subsp. *paracasei* |
| 43364 | *L. casei* subsp. *casei* | *L. paracasei* subsp. *paracasei* |
| 118 | *L. salivarius* | *L. salivarius* subsp. *salivarius* |
| 4231 | *L. salivarius* | *L. paracasei* subsp. *paracasei* |
| 42319 | *L. casei rhamnosus/pentosus* | ND |
| 42354 | *L. casei rhamnosus/pentosus* | ND |
| 42361 | *L. pentosus* | ND |

ND = Not Determined
*SDS-PAGE of cell wall proteins was courtesy of Bruno Pot (University of Ghent, Belgium)

Enzyme Activity Profiles

Enzyme activity profiles for the seventeen *Lactobacillus* sp. tested were carried out and the results were as follows:

None of the strains exhibited lipase, trypsin, α-chymotrypsin, β-glucuronidase, α-mannosidase or α-fucosidase activities and only weak β-glucosidase, N-acetyl-β-glucosaminidase activity was observed by three (43332, 43338, 43364) of the strains. All the strains tested were characterised by high acid phosphatase activity (means of 5.0) with phosphohydrolase and alkaline phosphatase activity being lower and more strain variable. Significant β-galactosidase activity was expressed by nine of the seventeen strains but little α-galactosidase activity was evident. Moderate to high levels of leucine, valine and cystine arylamidase activity was observed.

Antibiotic Sensitivity Profiles

Antibiotics of human clinical importance were used to ascertain the sensitivity profiles of selected *lactobacilli*. The *lactobacilli* tested were sensitive to ampicillin, amoxycillin, ceftaxime, ceftriaxone, ciprofloxacin, cephradine, rifampicin and chloramphenicol. They were also resistant to netilmicin, trimethoprim, nalidixic acid, amikacin, vancomycin and gentamicin. Variable sensitivity of the *lactobacilli* to teicoplanin and ceftizoxime was also observed.

EXAMPLE 2

Source and Maintenance of Strains

The *Lactobacillus* strains used were isolated as described in Example 1.

Human Gastric Juice

Human gastric juice was obtained from healthy subjects by aspiration through a nasogastric tube (Mercy Hospital, Cork, Ireland). It was immediately centrifuged at 13,000 g for 30 min to remove all solid particles, sterilised through 0.45 μm and 0.2 μm filters and divided into 40 ml aliquots which were stored at 4° C. and −20° C.

The pH and pepsin activity of the samples were measured prior to experimental use. Pepsin activity was measured using the quantitative haemoglobin assay (Gautam, S. and de La Motte, R. S., (1989) *Proteolytic enzymes, a practical approach. Chapter* 3. R. J. Beynon and J. S. Bond (eds.), IRL Press, Oxford University Press; (Dawson, R. M. (1969)

In *Data for Biochemical Research* 138. R. M. Dawson, D. C. Elliot and K. M. Jones (eds.), Clarendon Press, Oxford). Briefly, aliquots of gastric juice (1 ml) were added to 5 ml of substrate (0.7 M urea, 0.4% (w/v) bovine haemoglobin (Sigma Chemical Co.), 0.25 M KCl-HCl buffer, pH 2.0) and incubated at 25° C. Samples were removed at 0, 2, 4, 6, 8, 10, 20 and 30 min intervals. Reactions were terminated by the addition of 5% trichloroacetic acid (TCA) and allowed to stand for 30 min without agitation. Assay mixtures were then filtered (Whatman, No. 113), centrifuged at 14,000 g for 15 min and absorbance at 280 nm was measured. One unit of pepsin enzyme activity was defined as the amount of enzyme required to cause an increase of 0.001 units of $A_{280}$ nm per minute at pH 2.0 measured as TCA-soluble products using haemoglobin as substrate.

Growth of *lactobacilli* at Low pH

To determine whether growth of the *Lactobacillus* strains occurred at low pH values equivalent to those found in the stomach, overnight cultures were inoculated (1%) into fresh MRS broth adjusted to pH 4.0, 3.0, 2.0 and 1.0 using 1N HCl. At regular intervals aliquots (1.5 ml) were removed, optical density at 600 nm ($OD_{600}$) was measured and colony forming units per ml (cfu/ml) calculated using the plate count method. Growth was monitored over a 24–48 h period.

Survival of Strains in a Low pH Environment

Survival of the strains at low pH in vitro was investigated using two assays:

(a) Cells were harvested from fresh overnight cultures, washed twice in phosphate buffer (pH 6.5) and resuspended in MRS broth adjusted to pH 3.5, 3.0, 2.5 and 2.0 (with 1N HCl) to a final concentration of approximately $10^8$ cfU/ml for the *lactobacilli*. Cells were incubated at 37° C. and survival measured at intervals of 5, 30, 60 and 120 min using the plate count method.

(b) The *Lactobacillus* strains were propagated in buffered MRS broth (pH 6.0) daily for a 5 day period. The cells were harvested, washed and resuspended in pH adjusted MRS broth and survival measured over a 2 h period using the plate count method.

Survival of Microorganisms in Human Gastric Juice

To determine the ability of the *lactobacilli* to survive passage through the stomach, an ex-vivo study was performed using human gastric juice. Cells from fresh overnight cultures were harvested, washed twice in buffer (pH 6.5) and resuspended in human gastric juice to a final concentration of $10^{6-10^8}$ cfu/ml, depending on the strain. Survival was monitored over a 30–60 min incubation period at 37° C. The experiment was performed using gastric juice at pH ~1.2 (unadjusted) and pH 2.0 and 2.5 (adjusted using 1N NaOH).

Growth of *Lactobacillus* sp. at Low pH

The *Lactobacillus* strains (of human origin) grew normally at pH 6.8 and pH 4.5 reaching stationary phase after 8 h with a doubling time of 80–100 min. At pH 3.5 growth was restricted with doubling times increasing to 6–8 h. No growth was observed at pH 2.5 or lower, therefore, survival of the strains at low pH was examined.

Survival of *Lactobacillus* sp. at Low pH

Figure 2:
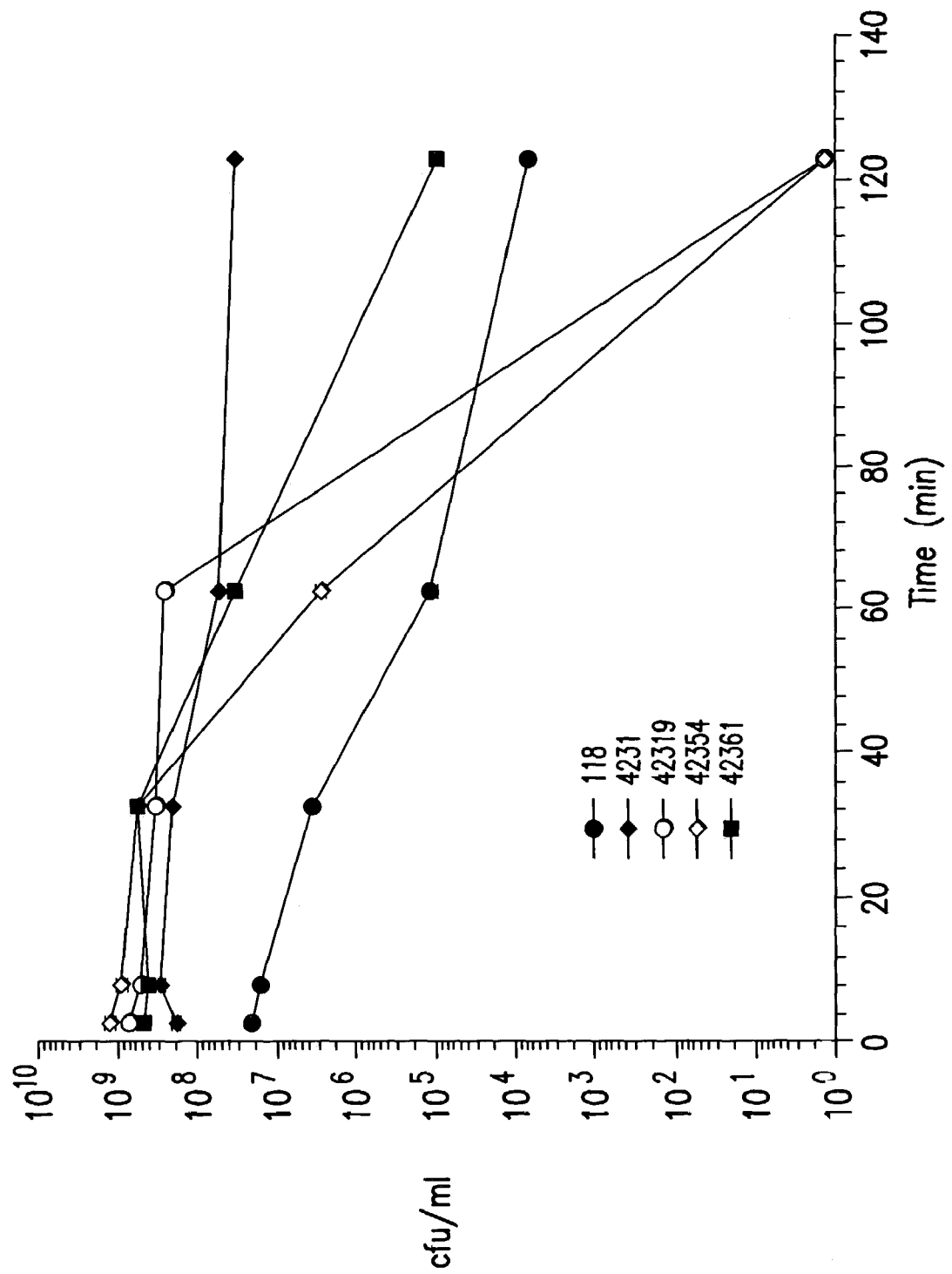
FIG. 2 is a graphic representation of the survival of washed cells of *Lactobacillus* strains (cfu/ml) in MRS broth, pH 2.0 versus time (min)

HCl-Adjusted Medium:

The *Lactobacillus* strains were generally resistant to pH values 3.5, 3.0 and 2.5. At pH 2.0, strain variation became apparent (see FIG. 1). The *Lactobacillus* strains of human origin survived with little log reduction for 1 h, however, *Lactobacillus* 118 had decreased by 2–4 log after 2 h incubation (see FIG. 2).

Human Gastric Juice:

To determine the ability of *Lactobacillus* strains to survive conditions encountered in the human stomach, viability of the strains was tested in human gastric juice at pH 1.2 and pH 2.5. Gastric juice adjusted to pH 2.5 was used to determine if factors other than pH are important in the inhibition of these strains by gastric juice. The strains according to the invention were recovered after 30 min incubation in gastric juice, pH 1.2, though at a reduced level. In gastric juice, pH 2.5, viability was approximately 100% in most cases, indicating that pH is the major inhibitory factor of gastric juice.

Inducible Acid Tolerance in *Lactobacillus* sp.

Figure 3:
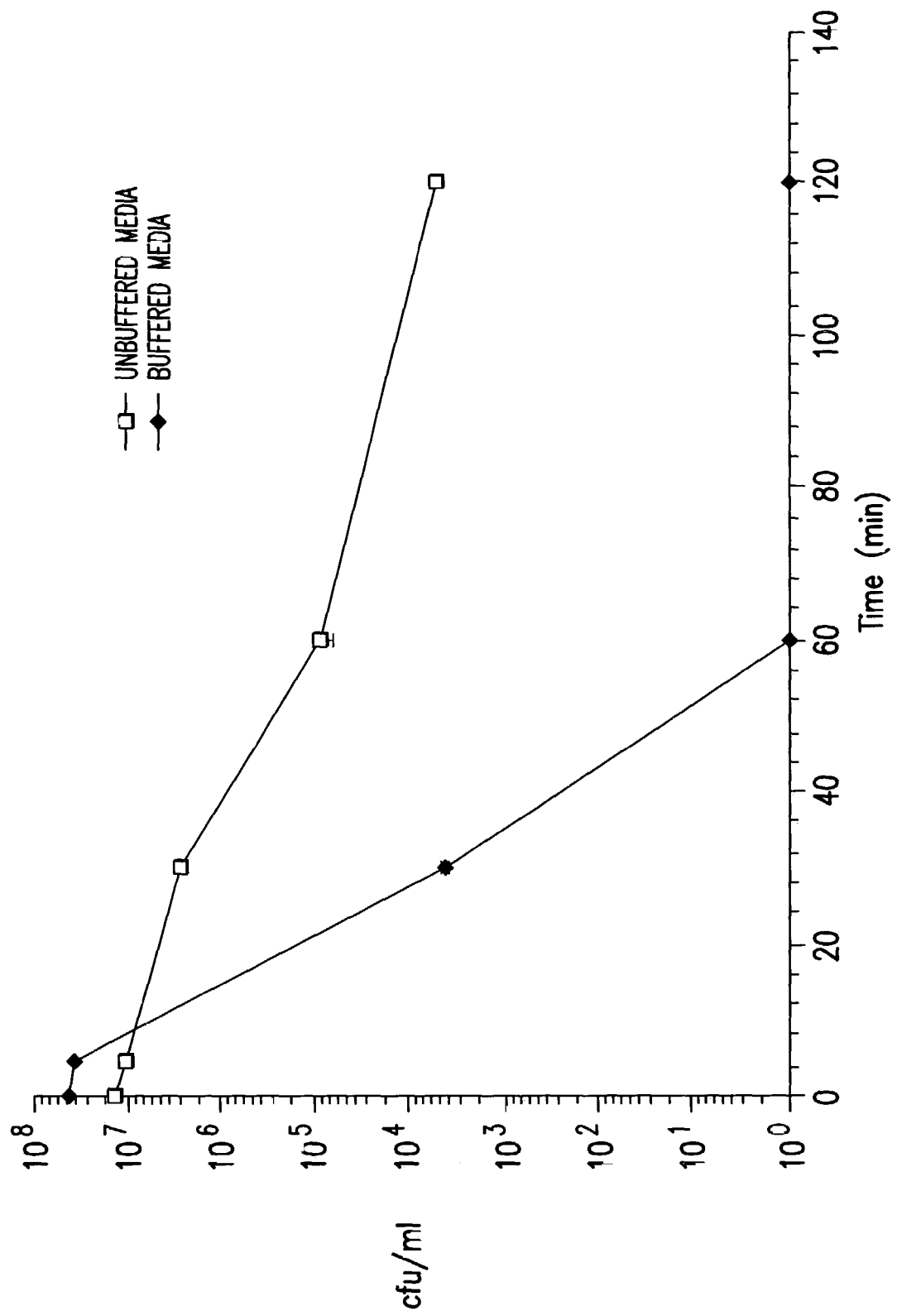
FIG. 3 is a graphic representation of the survival of *Lactobacillus* strain UCC 118 (cfu/ml) versus time (min) in unbuffered media and buffered media.

To determine strain survival at low pH after growth in a buffered carrier medium, the strains were grown continuously for one week at pH 7.0 and then challenged in MRS adjusted to pH 2.0–3.5 using 1N HCl. The *Lactobacillus* strains were resistant to pH values 3.5 and 3.0. At lower pH a distinct decrease in cell viability was observed. At pH 2.0 a rapid decline in cell number was recorded for example after 1 h incubation resulting in *Lactobacillus* sp. 118 and eight other strains not being recovered (see FIG. 3). After a further incubation of 1 h, five strains were recovered and these at levels of approximately $10^5$ cfu/ml.

It was observed in this study that prior growth of the *Lactobacillus* strains in buffered medium rendered them much more sensitive, in vitro, to low pH. Viable cells were not recovered after 30–60 min incubation at pH 2.0. When compared with survival of cells grown in unbuffered medium, it is clear that these strains possess the ability to adapt to a low pH environment after prior growth in pH environments of 4.0–4.5.

EXAMPLE 3

*Lactobacillus* strains used were isolated as described in Example 1.

Growth of Cultures in the Presence of Bovine and Porcine Bile

Fresh cultures were streaked onto MRS/TPY agar plates supplemented with bovine bile (B-8381, Sigma Chemical Co. Ltd., Poole) at concentrations of 0.3, 1.0, 1.5, 5.0 and 7.5% (w/v) and porcine bile (B-8631, Sigma Chemical Co. Ltd., Poole) at concentrations of 0.3, 0.5, 1.0, 1.5, 5.0 and 7.5% (w/v). Plates were incubated at 37° C. under anaerobic conditions and growth was recorded after 24–48 h.

Growth of Cultures in the Presence of Human Bile

Bile samples, isolated from several human gall-bladders, were stored at −80° C. before use. For experimental work, bile samples were thawed, pooled and sterilised at 80° C. for 10 min. Bile acid composition of human bile was determined using reverse-phase HPLC in combination with a pulsed amperometric detector according to the method of (Dekker, R. R. et al., (1991) *Chromatographia* 31 (11/12), 255–256). Human bile was added to MRS/TPY agar medium at a concentration of 0.3% (v/v). Freshly streaked cultures were examined for growth after 24 and 48 h.

Growth in the Presence of Individual Conjugated and Deconjugated Bile Acids

Human gall-bladder bile possesses a bile acid concentration of 50–100 mM, and dilution in the small intestine lowers this concentration to 5–10 mM (Hofmann, A. F., et al., (1983) *J. Clin. Invest.* 71, 1003–1022). Furthermore, under physiological conditions, bile acids are found as sodium salts. Therefore, cultures were screened for growth on MRS/TPY agar plates containing the sodium salt of each of the following bile acids (Sigma Chemical Co. Ltd., Poole): (a) conjugated form: taurocholic acid (TCA); glycocholic acid (GCA); taurodeoxycholic acid (TDCA); glycodeoxycholic acid (GDCA); taurochenodeoxycholic acid (TCDCA) and glycochenodeoxycholic acid (GCDCA); (b) deconjugated form: lithocholic acid (LCA); chenodeoxycholic acid (CDCA); deoxycholic acid (DCA) and cholic acid (CA). For each bile acid concentrations of 1, 3 and 5 mM were used. Growth was recorded after 24 and 48 h anaerobic incubation.

Detection of Bile Acid Deconjugation Activity

Both a qualitative (agar plate) and a quantitative (HPLC) assay were used to determine deconjugation activity.

Plate assay: All the cultures were streaked on MRS/TPY agar plates supplemented with (a) 0.3% (w/v) porcine bile, (b) 3 mM TDCA or (c) 3 mM GDCA. Deconjugation was observed as an opaque precipitate surrounding the colonies (Dashkevicz, M. P., et al. (1989) *Appl. Env. Microbiol.* 55(1), 11–16).

High Performance Liquid Chromatography:

Analysis of in vitro deconjugation of human bile was performed using HPLC (Dekker, R. R. et al., (1991) supra). Briefly, overnight cultures were inoculated (5%) into MRS/TPY broth supplemented with 0.3% (v/v) human bile and were incubated anaerobically at 37° C. At various time intervals over a 24 h period, samples (1 ml) were removed and centrifuged at 14,000 rpm for 10 min. Undiluted cell-free supernatant (30 μl) was then analysed by HPLC.

Isolation of *Lactobacillus* Variants with Increased Bile Acid Resistance

A single *Lactobacillus* colony was inoculated into MRS broth containing 0.3% porcine bile and incubated overnight. The culture was centrifuged at 14,000 rpm for 7 min, washed and resuspended in one quarter strength Ringers' solution. One hundred microlitres of a $10^{-3}$ dilution was spread-plated onto MRS agar plates consisting of a porcine bile gradient from 0.3 to 0.5%. The plates were incubated for 2 days at 37° C. Isolated colonies were picked from the agar sector containing 0.5% porcine bile, restreaked onto MRS supplemented with 0.5% porcine bile and incubated overnight. A number of colonies were then resuspended in one quarter strength Ringers' solution, diluted to $10^{-3}$ and plated onto gradient plates of increasing concentrations of porcine bile (0.5/1.0%, 1.0/1.5%, 1.5/2.0%, 2.0/2.5% and 2.5/3.0%). Colony morphology, Gram stains, wet mounts and catalase tests were performed on the colonies with increased resistance.

Resistance to Bile (Bovine, Porcine and Human)

All seventeen *Lactobacillus* strains tested were capable of growth (bile acid resistance) on three sources of bile used. It was observed that resistance to bovine bile was much higher than to porcine bile. *Lactobacillus* strains were resistant to concentrations up to and including 5.0% bovine bile and fourteen of the seventeen strains grew at 7.5%.

Porcine bile was more inhibitory to all strains as shown in Table 3.

TABLE 3

Growth of bacterial isolate in the presence of porcine bile

| STRAIN | % (w/v) PORCINE BILE | | | | | | |
|---|---|---|---|---|---|---|---|
|  | 0.0 | 0.3 | 0.5 | 1.0 | 1.5 | 5.0 | 7.5 |
| *Lactobacillus* sp. | | | | | | | |
| 1 | + | + | − | − | − | − | − |
| 4333 | + | + | − | − | − | − | − |
| 43310 | + | + | − | − | − | − | − |
| 43321 | + | + | − | − | − | − | − |
| 43324 | + | + | − | − | − | − | − |
| 43332 | + | + | + | + | + | − | − |
| 43336 | + | + | − | − | − | − | − |
| 43338 | + | + | − | − | − | − | − |
| 43348 | + | + | + | − | − | − | − |
| 43361 | + | + | + | + | + | + | − |
| 43362 | + | + | − | − | − | − | − |
| 43364 | + | + | − | − | − | − | − |
| 118 | + | + | + | + | − | − | − |
| 4231 | + | + | − | − | − | − | − |
| 42319 | + | + | + | + | + | + | + |
| 42354 | + | + | + | + | + | + | + |
| 42361 | + | + | + | + | + | + | + |

− = no growth
+ = confluent growth

Concentrations of 0.5% and higher inhibited the growth of ten of the seventeen *Lactobacillus* strains, whereas *Lactobacillus* sp. 42319, 42354 and 42361 grew to confluence at 7.5%.

Regardless of their bile resistance profiles in the presence of both bovine and porcine bile, the *Lactobacillus* strains grew to confluence at the physiological concentration of 0.3% (v/v) human bile.

Resistance to Individual Conjugated and Deconjugated Bile Acids

The *Lactobacillus* strains, when analysed specifically for their resistance to individual bile acids, grew well in the presence of taurine conjugated bile acids but growth in the presence of glycine conjugated bile acids was variable. *Lactobacillus* isolates grew to confluence on agar medium containing up to and including 5 mM of taunine conjugates TCA, TDCA and TCDCA. Of the glycine conjugates tested, GCDCA was the most inhibitory, with only four of the *Lactobacillus* sp. being able to grow at concentrations of 3 mM and 5 mM. GDCA was less inhibitory and GCA was the least inhibitory of the three glycine conjugates as shown in Table 4.

TABLE 4

Growth of bacterial isolates in the presence of glycine-conjugated bile acids

| | BILE ACIDS (mM) | | | | | | | | | | | |
|---|---|---|---|---|---|---|---|---|---|---|---|---|
| | GCDCA | | | | GDCA | | | | GCA | | | |
| STRAIN | 0 | 1 | 3 | 5 | 0 | 1 | 3 | 5 | 0 | 1 | 3 | 5 |
| *Lactobacillus* sp. | | | | | | | | | | | | |
| 1 | + | + | − | − | + | + | − | − | + | + | + | + |
| 4333 | + | + | − | − | + | + | + | + | + | + | + | + |
| 43310 | + | + | − | − | + | + | − | − | + | + | + | + |
| 43321 | + | + | − | − | + | + | − | − | + | + | + | + |

TABLE 4-continued

Growth of bacterial isolates in the presence of glycine-conjugated bile acids

| | BILE ACIDS (mM) | | | | | | | | | | | |
|---|---|---|---|---|---|---|---|---|---|---|---|---|
| | GCDCA | | | | GDCA | | | | GCA | | | |
| STRAIN | 0 | 1 | 3 | 5 | 0 | 1 | 3 | 5 | 0 | 1 | 3 | 5 |
| 43324 | + | + | − | − | + | + | − | − | + | + | + | + |
| 43332 | + | + | − | − | + | + | − | − | + | + | + | + |
| 43336 | + | + | − | − | + | + | + | − | + | + | + | + |
| 43338 | + | + | − | − | + | + | + | − | + | + | + | + |
| 43348 | + | + | − | − | + | + | − | − | + | + | + | + |
| 43361 | + | + | + | + | + | + | + | + | + | + | + | + |
| 43362 | + | + | − | − | + | + | + | − | + | + | + | + |
| 43364 | + | + | − | − | + | + | + | − | + | + | + | + |
| 118 | + | + | − | − | + | + | + | − | + | + | + | + |
| 4231 | + | + | − | − | + | + | + | − | + | + | + | + |
| 42319 | + | + | + | + | + | + | + | + | + | + | + | + |
| 42354 | + | + | + | + | + | + | + | + | + | + | + | + |
| 42361 | + | + | + | + | + | + | + | + | + | + | + | + |

In Table 4:
− = no growth;
+ = confluent growth
GCDCA = glycochenodeoxycholic acid;
GDCA = glycodeoxycholic acid;
GCA = glycocholic acid.

All strains grew on agar medium supplemented with 5 mM GCA, however, growth on GDCA was variable.

Growth in the presence of deconjugated bile acids was also tested. All strains were resistant to concentrations of 5 mM LCA. Fifteen of the seventeen *Lactobacillus* strains tested grew in concentrations of up to and including 5 mM DCA. Two strains, *Lactobacillus* sp. 1 and 43348, were sensitive to low concentrations of DCA (1 mM). Growth in the presence of CA was variable as shown in Table 5.

TABLE 5

Growth of bacterial isolates in the presence of unconjugated cholic acid (CA)

| | CHOLIC ACID (mM) | | | |
|---|---|---|---|---|
| STRAIN | 0 | 1 | 3 | 5 |
| *Lactobacillus* sp. | | | | |
| 1 | + | − | − | − |
| 4333 | + | − | − | − |
| 43310 | + | + | − | − |
| 43321 | + | − | − | − |
| 43324 | + | + | − | − |
| 43332 | + | + | − | − |
| 43336 | + | + | − | − |
| 43338 | + | + | + | + |
| 43348 | + | − | − | − |
| 43361 | + | + | + | + |
| 43362 | + | + | + | − |
| 43364 | + | + | + | + |
| 118 | + | + | + | − |
| 4231 | + | + | − | − |
| 42319 | + | + | + | + |
| 42354 | + | + | + | + |
| 42361 | + | + | + | + |

− = no growth;
+ = confluent growth

Only eight *Lactobacillus* strains were capable of growing on a concentration of 3 mM CA. Growth of the seventeen strains was not observed in the presence of 1 mM CDCA.

Deconjugation Activity of *Lactobacillus* sp.

From the growth studies it was observed that some of the strains possessed bile salt deconjugating activity and further investigation identified and three of the seventeen *Lactobacillus* strains (43361, 42319 and 42361) which were capable of deconjugating bile acids. This was demonstrated on agar medium supplemented with 0.3% porcine bile, TDCA (3 mM) and GDCA (3 nM). In all cases, deconjugation manifested itself as an opaque zone of precipitated deconjugated bile acid surrounding active colonies (Dashkevicz, M. P. and Feighner, S. D., (1989)*Appl. Env Microbiol.* 55(1), 11–16).

Bile acid deconjugation activity, observed on agar plates, was confirmed using human bile and HPLC analysis of breakdown products. Only conjugated bile acids were detected in the bile sample.

Induction of Bile Acid Resistance

A method was devised for the isolation of *Lactobacillus* strains with increased bile acid resistance. Two *Lactobacillus* strains (4333 and 43310) were chosen which were initially unable to grow in the presence of 0.5% porcine bile but which could grow at a concentration of 0.3% (see Table 3 above). Following continuous sub-culturing in the presence of increasing concentrations of porcine bile (0.3% to 3.0%), the resistance of strains 4333 and 43310 increased. Strains regularly sub-cultured on MRS agar maintained their induced bile resistance when restreaked onto MRS agar containing 3.0% porcine bile. Furthermore, induced bile resistant strains were subsequently able to deconjugate porcine bile.

With increasing concentrations of porcine bile, changes in colony morphology were observed with both strains tested. The colonies were irregular, flat to umbonate, and appeared grey and opaque in the presence of bile. However, when restreaked onto MRS agar, the colonies regained their original, smooth, creamy, convex, glistening appearance. (When viewed under the microscope both colony variants appeared as short rods, singly or in pairs). After prolonged sub-culturing in the absence of bile both strains still deconjugated and maintained resistance to high levels of porcine bile.

EXAMPLE 4

Growth and Maintenance of Cultures

The microorganisms screened for antimicrobial production were the seventeen strains listed in Table 3 and were isolated from the human intestinal tract as described in Example 1. All strains belonged to the UCC culture collection Cultures were maintained as frozen stocks at −20° C. in the appropriate growth medium and 40% glycerol. Lactobacilli were routinely cultured in deMann Rogosa Sharpe (MRS) medium at 37° C. under strict anaerobic conditions (BBL Gas Jars using the Merck Anaerocult A Gas Pak system).

The indicator microorganisms used in this Example, many of which are wildtype strains isolated in the Mercy Hospital, Cork, Ireland, were propagated in the following medium under the following growth conditions: *Staphylococcus* (37° C., aerobic), *Bacillus* (37° C., aerobic), *Pseudomonas* (30° C., aerobic), *Escherichia coli* (37° C., anaerobic), *Salmonella* (37° C., anaerobic) and *Listeria* (30° C., aerobic) in Tryptone Soya broth/agar supplemented with 0.6% yeast extract (TSAYE, Oxoid), *Campylobacter* (37° C., anaerobic), *Bacteroides* (37° C., anaerobic), *Helicobacter* (37° C., anaerobic), *Proteus* (37° C., anaerobic), Haemophilus (37° C.; anaerobic) and Pneumococcus (37° C., anaerobic) on Blood agar medium, Candida (37° C., aerobic) in YPD (Yeast (1%), Peptone (2%) and Dextrose (2%)) medium, Clostridium (37° C., anaerobic) in Reinforced Clostridial medium (RCM, Oxoid), Lactococcus (30° C., aerobic) in M17 medium (Oxoid), Streptococcus (37° C., anaerobic) in Todd Hewitt Medium (Oxoid) and Enterococcus (37° C., anaerobic) species in Brain Heart Infusion medium (BHI, Merck). All strains were inoculated into fresh growth medium and grown overnight before being used in experiments. Agar sloppies (overlays) and plates were prepared by adding 0.7% (w/v) and 1.5% (w/v) agar to the broth medium, respectively.

Detection of Antimicrobial Activity

Antimicrobial activity of the above strains was detected using the deferred method (Tagg J. R., et al (1976) Bacteriol. Rev 40,722–756). Indicators used in the initial screening were L. innocua, L. fermentum KLD, P. flourescens and E. coli V517. Briefly, the lactobacilli (MRS) were incubated for 12–16 h. Ten-fold serial dilutions were spread-plated (100 µl) onto MRS agar medium. After overnight incubation, plates with distinct colonies were overlayed with the indicator bacterium. The indicator lawn was prepared by inoculating a molten overlay with 2% (v/v) of an overnight indicator culture which was poured over the surface of the inoculated MRS plates. The plates were re-incubated overnight under conditions suitable for growth of the indicator bacterium. Indicator cultures with inhibition zones greater than 1 mm in radius were considered sensitive to the test bacterium.

This procedure was repeated with the supplementation of all agar media with 2% β-glycerophosphate buffer (Sigma Chemicals, Poole) and catalase (100 Units/ml; Sigma Chemicals, Poole), to eliminate antagonistic activity due to acid and hydrogen peroxide production, respectively. Inhibition due to bacteriophage activity was excluded by flipping the inoculated MRS agar plates upside down and overlaying with the indicator. Bacteriophage can not diffuse through agar.

Detection of Antimicrobial Activity in the Cell-Free Supernatant

To determine if antimicrobial activity is secretory in nature, lactobacilli (MRS) were grown in broth for 12–16 h, aliquots of culture (500 µl) were filter-sterilised (0.45 µm) and the cell-free supernatant was assayed for antimicrobial activity against the same four indicator strains. Activity of the cell-free supernatant was determined by a modification of the critical dilution method generally used for assay of bacteriocins (Mayr-Harting, A., et al., (1972) Methods in Microbiology Vol. 7A, 315–422). Two-fold serial dilutions were spotted (5 µl) onto freshly seeded lawns of L. innocua and L. fermentum KLD and the plates incubated appropriately. The titre was defined as the reciprocal of the highest dilution of inhibitor demonstrating complete inhibition of the indicator lawn and was expressed as activity units (AU) per milliliter (ml).

Ammonium Sulphate Precipitation of Antimicrobial Activity

The antimicrobial-producing strains, L. salivarius 1 and 118, were incubated in MRS broth (800 ml) under anaerobic conditions at 37° C. and cells were harvested at the time of maximum production of antimicrobial activity (usually 6–8 h with a 3% inoculum). The supernatant was treated with 40% ammonium sulphate for 1 h at 4° C. with constant agitation, held at 4° C. overnight and then centrifuged at 13,000 g for 30 min. The pellet and the pellicle (the layer at the top of the supernatant) were combined and dissolved in 20 ml of phosphate buffer, pH 6.5. The solutions were dialyzed against 5 l of phosphate buffer, pH 6.5, for 24 h at 4° C. with 2–3 changes of buffer. Solutions were then filter sterilised, assayed for antimicrobial activity and stored at 4° C. Ammonium sulphate precipitation of the cell-free supernatant at 70% and 100% was also carried out to increase specific activity.

Inhibitory Host Spectra

The inhibitory spectra of lactobacilli were determined by the method of Tagg, J. R. et al. (1976) as described above. Cell-free supernatant (CFS) and ammonium sulphate precipitated solution (APS) were also assayed for inhibitory activity against a wide range of Gram positive and Gram negative microorganisms. Overlays of each indicator were prepared on agar plates and allowed to dry. Spots (5 µl) of CFS and APS were placed on the seeded plates, allowed to dry and plates incubated overnight. The agar well-diffusion method was also employed for the inhibition of Helicobacter, Proteus, Bacteroides and Campylobacter sp. Agar plates were, either overlayed or swabbed with the indicator organism and allowed to dry. Wells (4 mm) were made in the agar plates and CFS (30–40 µl) was placed in the wells and allowed to diffuse through the agar for 20–40 min at room temperature prior to incubation for 24–48 h after which inhibitory zones were measured.

Sensitivity of Antimicrobials to Proteolytic Enzymes

Aliquots of CFS containing antimicrobial activity from individual producing strains were assayed for their sensitivity to proteolytic enzymes. Proteinase K (50 mg/ml, 50 mM $KH_2PO_4$, pH 7.5) and pronase E (50 mg/ml, 50 mM $KH_2PO_4$, pH 7.5) were individually incubated for 1 h at 37° C. with CFS at 3:1 ratio. Both enzyme-treated and untreated CFS were spotted (5 µl) onto freshly seeded indicator overlays agar and incubated appropriately.

Production of Antimicrobial Activity in Human Bile

Cultures 1 and 118 were spotted onto buffered MRS agar plates containing 0.3% human bile and incubated anaerobically at 37° C. overnight. They were overlayed with indicator strains and incubated for a further 12–18 h. Zones of inhibition greater than 1 mm were considered positive.

Detection of Antimicrobial Activity

The seventeen lactobacilli were screened for inhibitory activity using Ls. innocua, L. ferthentum KLD, P. fluorescens and E. coli as indicator microorganisms. When the test strains were inoculated on unbuffered MRS, inhibition of the four indicators was observed. Zones ranging in size from 1 mm to 5 mm were measured. Inhibition of Ls. innocua by the lactobacilli produced the largest zones.

Inhibition was not due to hydrogen peroxide since incorporation of catalase to MRS plates during the screening did not affect antimicrobial activity. Similarly, bacteriophage activity Was excluded as described above. When the lactobacilli were inoculated onto buffered MRS, very little inhibition towards the indicators was observed. There were two exceptions, L. salivarius 1 and 118 which produed zones of inhibition only marginally smaller than those produced in unbuffered MRS against the indicators.

Characterisation of Antimicrobial Activity

The antimicrobial activity of Lactobacillus sp. 1 and 118 was demonstrated to be secreted into the cell-free supernatant after 8 h of growth in MRS broth when assayed against Ls. innocua and B. coagulans 1761. CFS of 118 also exhibited inhibition towards *P. fluorescens* but this indicator was less sensitive than the previous two. Inhibition of *E. coli* by either ABP1 or ABP118 was not observed. Titres of up to 2000 AU/ml and 1000 AU/ml (using *Ls. innocua* and *L. fermentum* KLD, respectively) were measured. The inhibitory activities of *L. salivarius* 1 and 118, ABP1 and ABP118 respectively, were found to be proteinaceous, as no inhibition of sensitive indicators was observed with the protease-treated CFS. This indicates that both strains produce bacteriocins.

Inhibitory Host Spectra

The *lactobacilli* were seen to inhibit a wide range of both Gram positive and Gram negative indicator microorganisms in both buffered and unbuffered media. Little inhibitory activity was observed towards lactic acid bacteria, such as *Streptococcus* and other *lactobacilli*. The inhibitory spectra of *L. salivarius* 1 and 118 were quite broad. Little inhibition of lactic acid bacteria was observed, however, inhibition of *Staphylococcus*, *Bacillus*, *Salmonella*, *E. coli*, *Pseudomonas* and *Listeria* species was clearly visualized. This inhibition was also produced in the presence of physiological concentrations of human bile. CFS and APS of 1 and 118, ABP1 and ABP118 respectively, were also tested for inhibitory activity on a wide range of microorganisms and were very active against a number of Gram positive bacteria with ABP118 also being active against the Gram negative microorganism *Pseudomonas fluorescens*. The CFS were not very inhibitory towards other related lactic acid bacteria such as *Lactobacillus* or the *Leuconostoc*, *Lactococcus*, *Bifidobacterium* or *Pediococccus* species. Activity was seen against *Enterococcus* sp. Most noteworthy is the inhibition of strains of *Helicobacter pylori* and methicillin resistant *S. aureus* by ABP118 and ABP1 as shown in Table 6.

TABLE 6

Inhibitory spectra of ABP1 and ABP118, produced by *L. salivarius* 1 and 118, respectively

| Indicator strains | ABP118 | ABP1 |
|---|---|---|
| *Lactobacillus salivarius* 1 | − | − |
| *L. salivarius* 118 | − | − |
| *Enterococcus faecalis* | + | + |
| *E. faecium* | + | + |
| *Staphylococcus aureus* 1505 | + | + |
| *St. aureus* 1551 | + | + |
| *St. aureus* 1522 | + | + |
| *St. aureus* 1963 | + | + |
| *St. aureus* 2044 | +/− | +/− |
| *St. aureus* 771 | + | + |
| *St. aureus* 6511 | − | +/− |
| *St. aureus* MH | + | − |
| *St. aureus* 148 (methicillin resistant) | + | − |
| *St. carnosus* | + | + |
| *Bacillus subtilus* DW | + | + |
| *B. cereus* DW | + | − |
| *B. cereus* NCDO 577 | − | + |
| *B. thuringensis* 1146 | + | + |
| *B. megaterium* 1773 | + | + |
| *B. coagulans* 1761 | + | + |
| *Clostridium tyrobutyricum* 1756 | +/− | +/− |
| *C. tyrobutyricum* 885A | +/− | +/− |
| *C. tyrobutyricum* 1757 | +/− | +/− |
| *C. tyrobutyricum* 1729 | +/− | +/− |
| *C. butyricum* 7423 | +/− | +/− |
| *Pneumococcus* sp. 788 | +/− | +/− |
| *Pneumococcus* sp. 904 | +/− | +/− |
| *Haemophilus* sp. | − | − |
| *Pseudomonas fluorescens* | + | − |
| *P. fragi* | + | − |
| *Escherichia coli* 1266 | − | − |

TABLE 6-continued

Inhibitory spectra of ABP1 and ABP118, produced by *L. salivarius* 1 and 118, respectively

| Indicator strains | ABP118 | ABP1 |
|---|---|---|
| *E. coli* V517 | − | − |
| *E. coli* | − | − |
| *Enterobacter* sp. 736 | − | − |
| *Salmonella typhimurium* LT2 | − | − |
| *S. typhimurium* | − | − |
| *S. enteriditis* | − | − |
| *Helicobacter pylori* Pu25 | − | − |
| *H. pylori* Pu35 | + | − |
| *H. pylori* Pu37 | − | − |
| *Campylobacter* sp. | − | − |
| *Bacteroides* sp. 28644-1 | + | nd |
| *Bacteroides* sp. 28644-2 | + | nd |
| *Proteus* sp. 776 | − | − |
| *Proteus* sp. 778 | − | − |
| *Proteus* sp. 889 | − | − |
| *Listeria monocytogenes* | + | + |
| *Ls. innocua* | + | + |

In Table 6
+ = inhibition of indicator strains;
− = no inhibition of indicator strains;
+/− = slight inhibition of indicator strains;
nd = not determined

EXAMPLE 5

Growth and Maintenance of Cultures

*Lactobacillus salivarius* 118 was isolated, identified and cultured from the human intestinal tract as described in Example 1.

The indicator microorganisms used in this Example were propagated in Tryptone Soya broth supplemented with 0.6% yeast extract (TSAYE, Oxoid) under the following growth conditions, *Bacillus* (37° C., aerobic), *Escherichia coli* (37° C., anaerobic), *Salmonella* (37° C., anaerobic) and *Listeria* (30° C., aerobic). All strains were inoculated into fresh growth medium and grown overnight before being used in experiments. Agar sloppies (overlays) and plates were prepared by adding 0.7% (w/v) and 1.5% (w/v) agar to the broth medium, respectively.

Detection of Antimicrobial Activity

*L. salivarius* 118 was grown for 12–16 h in MRS broth and the culture centrifuged at 14,000 g for 10 min. Cell-free supernatant (CES) was spotted (5–10 μl) onto freshly seeded lawns of *Listeria innocua* and *Bacillus coagulans* 1761. Zones of inhibition were measured.

Activity of the CFS was assayed for by a modification of the critical dilution method generally used for assay of bacteriocins (Mayr-Harting et al., (1972) supra). Serial dilutions were spotted (5 μl) onto freshly seeded lawns of *Ls. innocua* and *B. coagulans* 1761 and the plates incubated appropriately. The titre was defined as the reciprocal of the highest dilution of inhibitor demonstrating complete inhibition of the indicator lawn and was expressed as activity units (AU) per milliliter (ml).

Ammonium Sulphate Precipitation of the Cell-Free Supernatant Containing ABP118

*L. salivarius* 118 was grown in broth (800 ml) under anaerobic conditions at 37° C. and cells were harvested after 6–8 h incubation. The supernatant was concentrated using 40% ammonium sulphate for 1 h at 4° C. with constant agitation, held at 4° C. overnight and then centrifuged at 13,000 g for 30 min. The pellet and the pellicle (the layer at the top of the supernatant) were collected and dissolved in a small volume of phosphate buffer, pH 6.5. The solutions were dialyzed against 5 l of phosphate buffer, pH 6.5, for 24 h at 4° C. with 2–3 changes of buffer. Solutions were then filter sterilised, assayed for antimicrobial activity and stored at 4° C. This was used in the following experiments unless otherwise stated.

Factors Influencing Growth of L. salivarius 118 and Production of ABP118 pH;

L. salivarius 118 was grown up overnight in MRS broth (50 ml) at 37° C. and then inoculated (2%) into MRS broth (1.5 l) in a fermentation vessel (Model 502D; L.H. Fermentation, Stoke Poges, Bucks.) which was connected to an automatic pH controller, at 37° C., with gentle agitation (200 rpm) and continuously flushed with 5% $CO_2$. The following pH conditions were imposed in four different experiments: (1) pH 5.5; (2) pH 5.0; (3) pH 4.5 and (4) pH 4.0 and pH was maintained using 8% ammonium hydroxide solution during the experiment. At regular intervals pH, $OD_{600}$, bacterial counts (cfu/ml) and antimicrobial activity (AU/ml) were recorded over a 24 h period.

Growth Medium:

Various laboratory media were tested for their ability to support both the growth of L. salivarius 118 and the production of ABP118. These included MRS, Brain Heart Infusion (BHI), GM17 and Tryptone Soya broth supplemented with 0.6% yeast extract (TSBYE). The effects of the elimination of media constituents from MRS broth on growth and antimicrobial production was also evaluated. The ingredients eliminated included, a) Tween 80, b) Peptone, c) Yeast extract, d) Beef extract, e) Tween 80 and beef extract and f) Tween 80, beef extract and peptone.

Growth and antimicrobial production was also monitored in, 13.5% skim milk; 13.5% skim milk supplemented with 0.6% yeast extract; 13.5% skim milk supplemented with 2% glucose and 13.5% skim milk supplemented with 2% glucose and 0.6% yeast extract, and in MRS broth supplemented with 0.3% human bile (obtained from human gallbladder and sterilised at 80° C. for 10 mins). At regular intervals, pH, $OD_{600}$, bacterial counts and antimicrobial activity were recorded. All growth curves were carried out at 37° C. under anaerobic conditions.

pH and Temperature Stability of ABP118

ABP118 was tested for its stability in both alkaline and acidic conditions. pH of the active CFS was adjusted from 1 to 10 using 1N NaOH and HCl. Solutions were filter-sterilised and after incubation for 1 h at room temperature, activity was calculated before and after adjustment using Ls. innocua as the indicator. The pH-adjusted solutions were then readjusted to pH 7 using 1N NaOH and HCl and again incubated for 1 h at room temperature and assayed for AU/ml. Controls used were MRS broth adjusted to the same pH values.

To determine the temperature stability of ABP118, aliquots (10 ml) were incubated at various temperatures for different time periods and activity was calculated before and after incubation, using the indicator Ls. innocua.

Sensitivity of ABP118 to the Actions of Enzymes, Detergents and Organic Solvents To determine the nature and stability of the antimicrobial activity, ABP118 was incubated with the following enzymes (in a 3 to 1 ratio) for 30–60 min and assayed for antimicrobial activity: proteinase K (50 mg/ml, 50 mM $KH_2PO_4$, pH 7.5); pronase E (50 mg/ml, 50 mM $KH_2PO_4$, pH 7.5); trypsin (50 mg/ml, 67 mM $Na_2PO_4$, pH 7.6); α-chymotrypsin (50 mg/ml. 80 mM Tris, pH 7.8); α-amylase (50 mg/ml, 20 mM $Na_2PO_4$, pH 6.9); protease-free lipase (50 mg/ml); ficin (10 mM $KH_2PO_4$, pH 7.0); catalase (50,000 U/ml $dH_2O$); lysozyme (10 mg/ml, 25 mM Tris-HCl, pH 8.0); alkaline phosphatase (80 mM Tris-HCl, pH 8.0); pepsin (10 mM HCl); phospholipase C (10 mM $KH_2PO_4$, pH 7.0) and papain (10 mM KH2PO4, pH 7.0). Aliquots (5 µl) of each of these solutions were spotted onto plates already seeded with Ls. innocua and B. coagulans 1761. Controls included buffer and enzyme, and ABP118.

ABP118 was also treated with a number of solvents and detergents for 1–2 h at 37° C. The solvents used were, 5% β-mercaptoethanol; 10% chloroform; 10% acetone; 10% isopropanol; 25% ethanol; 50% acetonitrile; 10% butanol and 50% dichloromethane. The detergents used included, Tween 80 (1%), Tween 20 (1%), Triton X-100 (1%), N-laurylsarcosine (1%) and SDS (0.1% and 1%). After incubation the solutions were either dialyzed, vaccum-, or freeze-dried and assayed for activity.

Enzymatic Activity of ABP118

ABP118 was applied to the ZYM kit (BioMerieux, France) which is used to assay for constitutive enzyme activity (see Example 1 above). To assay for haemolytic and proteolytic activity, ABP118 was spotted (10 µl) on blood agar and skim milk agar plates, respectively. Reactions were recorded after 24 h and 48 h incubation at 37° C.

Determination of Molecular Size of ABP118 by Ultrafiltration

The size of ABP118 was estimated from the cell-free supernatant (CFS) and ammonium sulphate precipitated solution (APS; see Example 4 above) of a L. salivarius 118 culture. Aliquots were ultrafiltered through various membranes (Amicon Inc., Mass., USA) including 100-, 30-, 10- and 3 kDa molecular exclusion sizes. Bacteriocin activity was determined in retained and flowthrough fractions.

Isolation of Variants Deficient in ABP118 Production

MRS broth (100 ml) inoculated (2%) with L. salivarius 118 was incubated at temperatures above that allowing optimal growth (40°, 42° and 45° C.). After 36–48 h growth, broths were serially diluted and spread-plated (100 µl) onto MRS agar. Colonies were then replica-plated onto MRS agar and MRS agar supplemented with 2% β-glycerophosphate buffer. Plates were overlayed with sensitive indicator (B. coagulans 1761) and non-inhibiting colonies were streaked out for purity and stocked in 40% glycerol at −20° C. Growth rates of strains and carbohydrate fermentation profiles (API 50CHL) were recorded and compared to that of the wildtype L. salivarius 118.

Co-Culturing Studies

Associative growth of L. salivarius 118 and Salmonella (S. typhimurium and S. enteriditis) was studied in modified MRS medium (without sodium acetate). Indicator and producer strains were inoculated in 1:1 ratio. As a control, strains were also grown singly in the same medium. Inoculated media were incubated anaerobically at 37° C. Samples were taken at regular intervals to determine cell growth (cfu/ml). Salmonella-Shigella (Oxoid) and MRS (Oxoid) medium were used for the selective enumeration of Salmonella and Lactobacillus, respectively. Tryptone soya agar supplemented with 0.6% yeast extract (TSAYE) was used to obtain total plate counts. Salmonella were also co-cultured 1:1 with a non-ABP 118-producing variant of the wildtype L. salivarius 118.

Nature of the Antimicrobial Compound ABP118

The inhibitor, ABP118, is protein in nature as it is neutralised by protease enzymes such as pronase E, trypsin and pepsin as shown in Tables 7 and 8 and is also actively secreted in the supernatant.

TABLE 7

Sensitivity of ABP118 to proteolytic and non-proteolytic enzymes

| | |
|---|---|
| Pronase E | + |
| Proteinase K | + |
| Trypsin | + |
| α-chymotrypsin | + |
| Ficin | + |
| Papain | + |
| Pepsin | + |
| Lipase (protease-free) | − |
| Catalase | − |
| Alkaline phosphatase | − |
| Phospholipase C | − |
| Lipoprotein lipase | − |

+ = ABP118 sensitive to enzyme treatment
− = ABP118 resistant to enzyme treatment

TABLE 8

Effect of protease treatment on ABP118 activity

| Treatment | Activity of ABP118 (AU/ml) |
|---|---|
| ABP118 (no treatment) | 2000 |
| ABP118 + proteinase K at 37° C. × 30 min | 0 |
| ABP118 at 100° C. × 15 min | 2000 |
| ABP118 + [proteinase K at 100° C. × 15 min] at 37° C. × 30 min | 2000 |
| [ABP118 + proteinase K] at 100° C. × 15 min | 2000 |
| ([ABP118 + proteinase K] at 37° C. × 30 min) at 100° C. × 15 min | 0 |

Protease eliminated antimicrobial activity which was irretrievable after inactivation of the protease. ABP118 does not appear to have a lipid component based on the fact that lipase had no effect on activity (see Table 7). The compound was active in pH range 1–10 with no reduction in activity (against Ls. innocua) observed. It is a heat stable protein retaining 100%. activity for at least 1 h at 100° C. and with only a 50% loss following severe heat treatment by autoclaving as shown in Table 9.

TABLE 9

Temperature stability profile of ABP118

| Treatment | Activity of ABP118 (AU/ml) | % Reduction of ABP118 activity |
|---|---|---|
| Untreated | 2000 | 0 |
| 121° C. × 15 min | 1000 | 50 |
| 100° C. × 1 h | 2000 | 0 |
| 100° C. × 2 h | 500 | 75 |
| 63° C. × 30 min | 2000 | 0 |
| 60° C. × 1 h | 2000 | 0 |
| 60° C. × 2 h | 2000 | 0 |
| 37° C. × 1 week | 500 | 75 |
| 30° C. × 1 week | 1000 | 50 |
| 15° C. × 1 week | 2000 | 0 |
| 4° C. × 4 months | 2000 | 0 |

The inhibitor ABP118 was also very stable when stored at 4° C. for 4 months with no loss in activity. Treatment of the compound with a number of organic solvents and detergents did not result in decreased activity as shown in Table 10.

TABLE 10

Stability of ABP118 in organic solvents and detergents

| Treatment | Activity of ABP118 (AU/ml) |
|---|---|
| Untreated | 2000 |
| Organic solvents | |
| Chloroform (10%) | 2000 |
| Acetone (10%) | 2000 |
| Isopropanol (10%) | 2000 |
| Ethanol (25%) | 2000 |
| Acetonitrile (50%) | 2000 |
| Butanol (10%) | 2000 |
| Dichloromethane (50%) | 2000 |
| β-mercaptoethanol (5%) | 2000 |
| Detergents | |
| Tween 80 (Trade Mark) (1%) | 2000 |
| Tween 20 (Trade Mark) (1%) | 2000 |
| Triton X (Trade Mark) – 100 (1%) | 2000 |
| N-laurylsarcosine (1%) | 2000 |
| SDS (0.1%) | 2000 |
| SDS (1.0%) | 1500 |

When ABP118 was spotted on skim milk agar, no proteolysis was observed over a 24 h incubation period at 37° C. or at room temperature. Reactions on blood agar (rabbit and horse) were less conclusive. Though small zones of lysis were recorded, small zones of lysis were also observed when concentrated MRS broth was spotted on the blood agar plates. The ZYM kit, which assays for a wide range 110 of enzymatic activity including esterase and lipase activity revealed no obvious enzymatic activity for ABP118. Ultrafiltration of culture supernatant and partially-purified ABP118 showed that the majority of activity was present in the retentate with the 100-kDa cutoff membrane and all activity was retained on the 30-kDa cutoff membrane.

Kinetics of ABP118 Production

Figure 4:
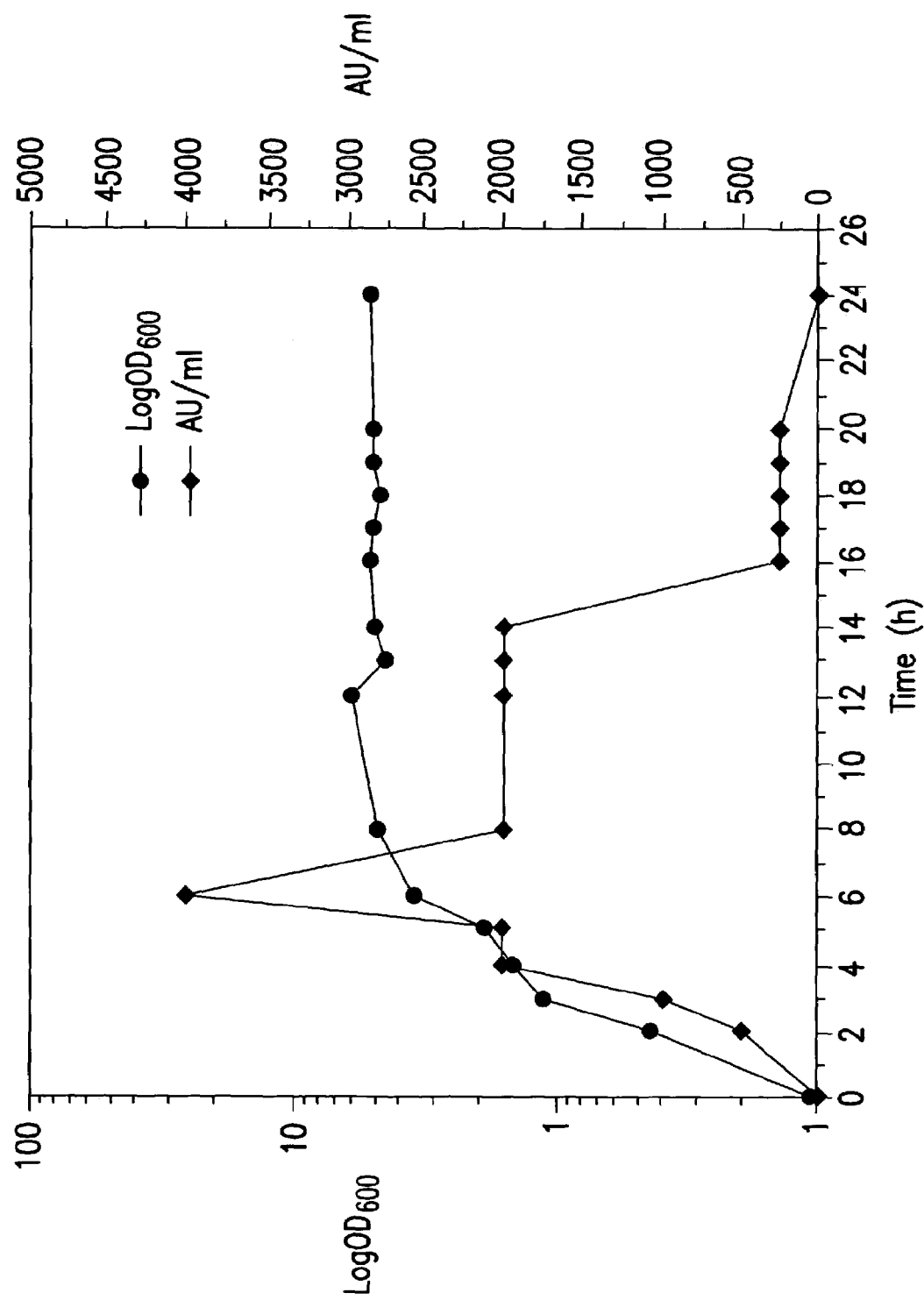
FIG. 4 is a graphic representation indicating growth of *L. salivarius* UCC 118 (log OD 600) and production of ABP118 (AU/ml) versus time (h)
Figure 5A:
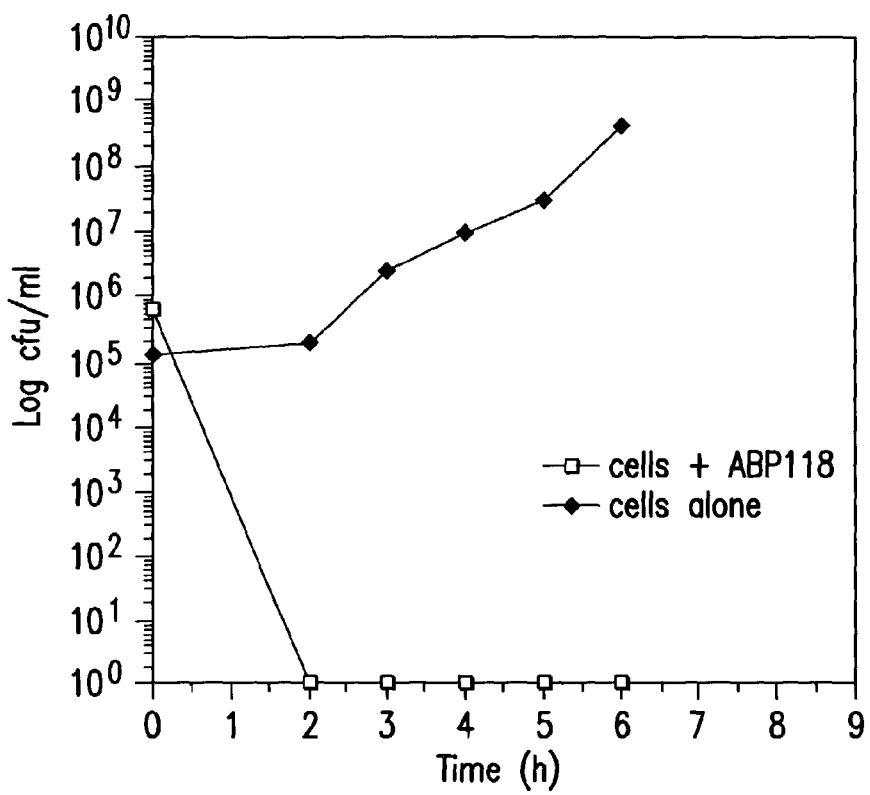
FIG. 5A–FIG. 5D are a graphic representation of the bactericidal effect of ABP118 (5000 AU/ml) on washed (and resuspended in buffer) and unwashed log-, and stationary-phase cells of *Bacillus coagulans* 1761.
Figure 5B:
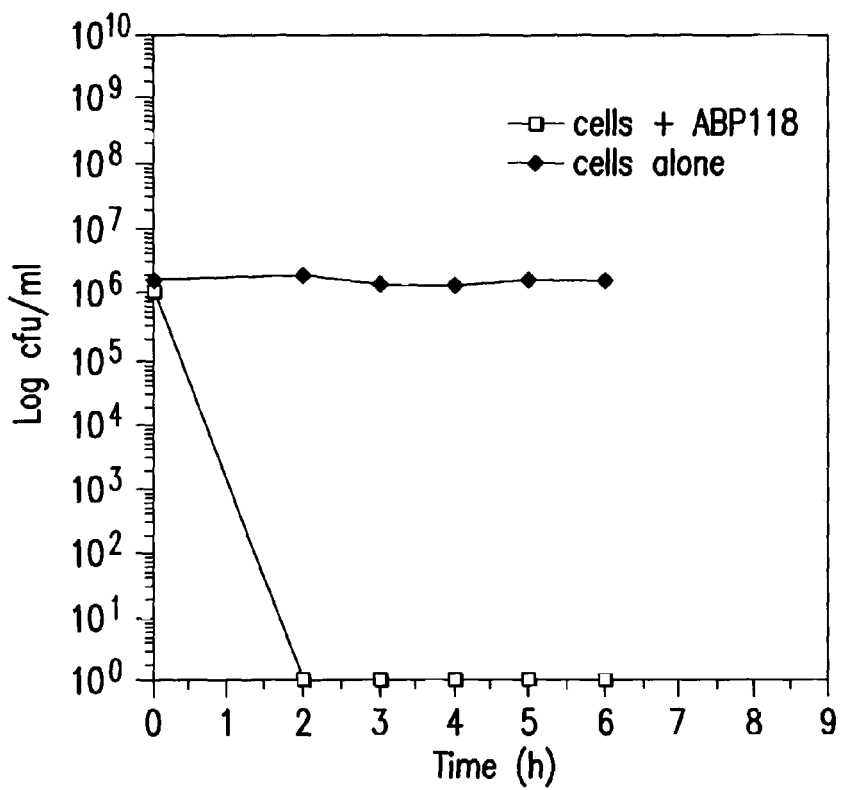
Figure 5C:
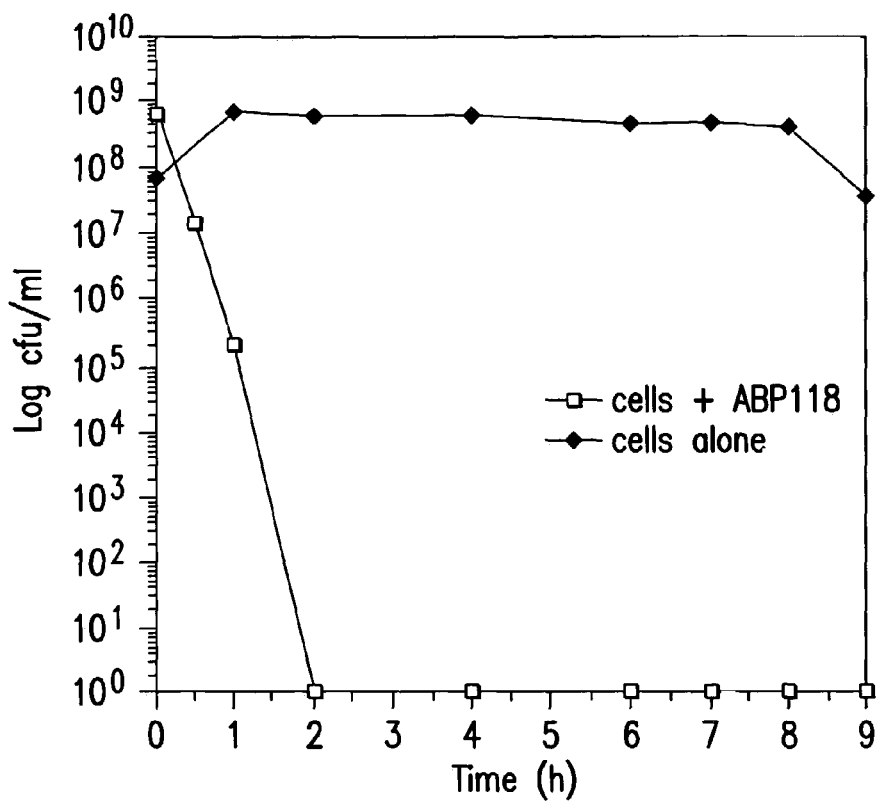
Figure 5D:
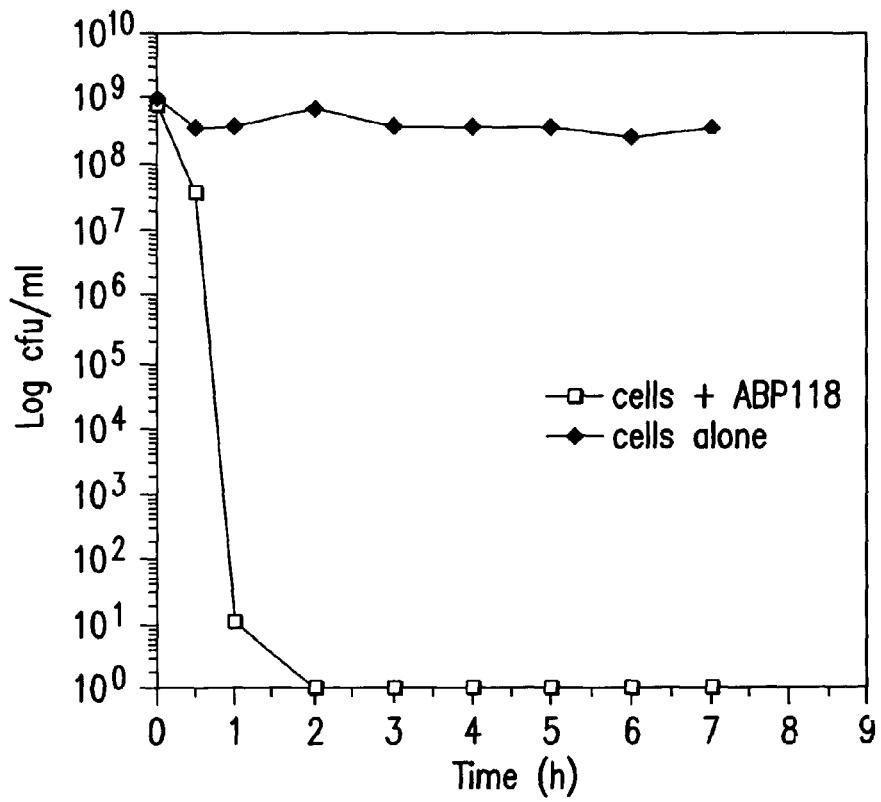

The production of ABP118 was dependent on the phase of growth. The kinetics of growth and antimicrobial production by L. salivarius 118 is illustrated in FIG. 4. Production of ABP118 was maximal during the logarithmic phase with a reduction in ABP118 concentration during the stationary phase. Maximum concentration of ABP118 activity was found when pH was controlled at pH 5.5 with up to 4000 AU/ml being produced after 3–4 h when biomass was quite high. At pH 4.0 growth of the culture was reduced and ABP118 was not detected. These studies indicate that ABP118 is produced only by growing and not by non-growing cells.

Of the four laboratory media tested, MRS and BHI were the two most suitable for support of production of large concentrations of ABP118. To determine if a less complex medium would still support production of ABP118, the effect of Tween 80, yeast extract and peptone sources was assayed. Results show that in the absence of any one of these, the concentration of ABP118 reached only 50% that of concentration produced in MRS broth. However, ABP118 activity remained more stable in the medium lacking yeast extract than in any other media tested.

The ability of a skim milk-based medium to act as a suitable carrier to support the growth of L. salivarius 118 and production of ABP118 was investigated. Growth in skim milk, skim milk plus yeast extract, and skim milk plus glucose was quite poor. The pH did not go lower than 5.7 after 12 h incubation and little if any ABP118 activity was detected. However, when L. salivarius 118 was grown in skim milk plus yeast extract plus glucose, pH reached a value of 4.4 and 3.87 after 12 and 24 h incubation, respectively. ABP118 activity was detected after 2 h at low levels and the majority of ABP118 (10,000 AU/ml against *B. coagulans* 1761) was produced by late-log to early-stationary phase of growth. It was also observed that the milk was beginning to clot after 10 h incubation.

The growth rate of *L. salivarius* 118 in 0.3% human bile was equivalent to the growth rate in MRS broth. However, only one third of the concentration of ABP118 was produced.

EXAMPLE 6

Detection of Antimicrobial Activity

Spot Assay:

*L. salivarius* 118 was grown in MRS broth and the culture centrifuged at 14,000 g for 10 min. Cell-free supernatant (CFS) was spotted (5–10 µl) onto freshly seeded lawns of indicator, incubated and zones of inhibition recorded. Activity of the cell-free supernatant was assayed for by a modification of the critical dilution method generally used for assay of bacteriocins (Mayr-Harting et al., (1972) supra). Serial dilutions were spotted (5l1) onto freshly seeded lawns of *Ls. innocua*, *B. coagulans* 1761 and *L. fermentum* KLD and the plates incubated appropriately. The titre was defined as the reciprocal of the highest dilution of inhibitor demonstrating complete inhibition of the indicator lawn and was expressed as activity units (AU) per milliliter (ml).

Microtitre Plate Assay:

Bacteriocin activity was measured during the purification procedure by the microtitre plate assay as described by Holo, H., et al. (1991) *J. Bacteriol.* 173, 3879–3887. Two-fold serial dilutions of bacteriocin extracts (50 µl) in TSAYE broth were prepared in microtitre plates (Greiner GmbH, Frickenhausen). One hundred and fifty microliters of fresh indicator culture ($A_{600}$~0.1) and 50 µl of TSAYE were added and the plates incubated at 37° C. Growth of the indicator strain was measured spectrophotometrically at 600 nm. One bacteriocin unit was defined as the amount of bacteriocin causing 50% growth inhibition (50% of the turbidity of the control culture without bacteriocin) in this assay.

Bacteriocin Purification

Ammonium Sulphate Precipitation:

*L. salivarius* 118 was grown to the late logarithmic phase in 2 l of MRS broth (Oxoid) and centrifuged at 12,000 rpm for 20 min. Ammonium sulphate (300 g/l) was added to the cell-free supernatant, stirred at 4° C. for 1 h, and centrifuged at 8,000 rpm for 30 min. The pellet and pellicle (floating solid material) were combined and dissolved in 100 ml $H_2O$ (Fraction I).

Hydrophobic Interaction Chromatography:

Fraction I was mixed with 10 g of amberlite XAD-16 (Supelco) for 30–45 min applied to a column and washed once with $H_2O$ (100 ml) and then twice with 40% ethanol (100 ml). The bacteriocin was eluted from the column with 100 ml (10×10 ml) of 70% isopropanol-10 mM HCl (Fraction II).

Cation Exchange Chromatography:

Fraction II was adjusted to pH 2–3 with $H_2O$+0.1% trifluoroacetic acid (TFA) and immediately applied to a 2 ml S-Sepharose Fast Flow cation exchange column previously equilibrated with 5 mM sodium phosphate buffer, pH 5.4 (buffer A). After subsequent washing with 40 ml of buffer A, the bacteriocin was eluted with 20 ml of 1 M NaCl in buffer A (Fraction III).

$C_2/C_{18}$ Reverse-Phase FPLC:

Fraction III was applied to a $C_2/C_{18}$ reverse-phase FPLC column (Pep RPC) equilibrated with isopropanol containing 0.1% TFA, solution A. The bacteriocin was eluted with a linear gradient ranging from 30–37% solution A for 40 min, followed by a gradient 37–100% solution A for another 5 min. The flow rate was 0.5 ml/min and 1 ml fractions were collected. Each fraction was tested for activity using the microtitre plate assay. Fractions with high bacteriocin activity were mixed and rechromatographed on the reverse-phase column.

Amino Acid Composition and Sequence Analysis

The purified bacteriocin was hydrolyzed and analyzed on an amino acid analyzer as described previously (Fykse, E. M., et al., (1988) *Biochem J.* 256, 973–980). The amino acid sequence was performed by Edman degradation with an Applied Biosystems model 477A automatic sequencer with an on-line 120A phenylthriohydantoin amino acid analyser (Cornwell, G. G., et al., (1988) *Biochem. Biophys. Res. Commun.* 154, 648–653) The C-terminal part of the sequence was obtained after cleavage of the bacteriocin with cyanogen bromide (CnBr) (Sletten, K., et al., (1974) *Eur. J. Biochem.* 41, 117–125).

Mode of Action of ABP118

Adsorption Assays:

Ability of ABP118 to adsorb to the cell wall of sensitive and resistant strains was investigated. Briefly, three overnight cultures of *Ls. innocua*, *L. salivarius* UCC 118, *L. fermentum* KLD, *E. coli.* 1266 and *B. coagulans* 1761 were each subcultured in fresh broth (20 ml) and grown to mid-logarithmic phase. Cells were harvested by centrifugation, washed twice in 50 mM sodium phosphate buffer, pH 6.5, and resuspended in buffers pH 4.0, 6.0 and 8.0 containing 2000 AU/ml of ABP118. The mixtures were incubated at 37° C. for 2 h. The cells were then removed by centrifugation and the antimicrobial titre of the supernatant was determined. Controls included incubation of 2000 AU/ml of ABP 118 with no cells and cells with no ABP 118 added.

Bactericidal Versus Bacteriostatic Action of ABP 118:

Duplicates of *Ls. innocua*, *L. fermentum* KLD and *B. coagulans* 1761 were grown to log-phase ($OD_{600}$, 0.2–0.5). To one set of cells 5000 AU/ml of ABP118 was added. The second set of cells were washed twice and resuspended in phosphate buffer, pH 6.5 prior to the addition of 5000 AU/ml of ABP118. Growth (cfu/ml) under the appropriate conditions, was monitored for a further 7–8 h. This experiment was repeated using stationary-phase cells.

Effect of ABP118 on DNA, RNA and Protein Synthesis of Sensitive Cells:

The sensitive indicator *B. coagulans* 1761 was inoculated (3% (v/v)) into TSAYE growth medium and grown to early log phase (3–4 h) at 37° C. The culture was divided in two. To one half 5000 AU/ml of antimicrobial compound was added while an equivalent volume of growth medium was added to the other half. Each half was then supplemented with a radiolabelled substrate. The following substrates (New England Nuclear Corps.) were used: [5,6-$^3$H]uridine (39.6 Ci/mmol) at 5 µCi/ml; methyl [$^3$H]thymidine (6.7 Ci/mmol) at 5 µCi/ml and L-[$^{35}$S]methionine (1175 Ci/mmol) at 5 µCi/ml. At regular intervals, samples were removed from the cultures and growth medium added (pH 5.8). Each sample was then supplemented with 15% trichloroacetic acid (TCA), mixed4 well and incubated on ice for 18 h. The samples were then filtered through glass fiber filters and washed with 5% TCA and dried. Filters were placed in scintillation vials with Beckman Ecolite scintillatant and counted in a Beckman liquid scintillation counter.

Purification of ABP118

ABP118, which is produced in the log-phase of growth (see Example 5), was concentrated 20-fold from culture media, by; ammonium sulphate precipitation (Fraction I) resulting in a 292-fold increase in specific activity with a recovery of 250% as shown in Tables 11 and 12.

TABLE 11

Purification of ABP118

| Purification stage | Vol. (ml) | Total* $A_{280}$ | Total act. (BU) |
| --- | --- | --- | --- |
| Culture supernatant Fraction | 2000 | 54,800 | 5,120,000 |
| I Ammonium suphate ppt. | | 470 | 12,800,000 |
| II Hydrophobic (interaction (XAD-16) | | 51 | 192,000 |
| III Cation exchange | | 5.98 | 6,400 |
| IVC$_2$/C$_{18}$ Reverse-phase FPLC | 1.5 | 0.192 | 2,400 |

*Total $A_{280}$ equals the optical density at 280 nm multiplied by the volume in ml.

TABLE 12

Purification of ABP118

| Purification stage | Sp. act.* | Increase in sp. act. (fold) | Yield (%) |
| --- | --- | --- | --- |
| Culture supernatant Fraction | 93 | 1 | 100 |
| I Ammonium suphate ppt. | 27,234 | 292 | 250 |
| II Hydrophobic (interaction (XAD-16) | 3,765 | 40 | 3.75 |
| III Cation exchange | 1,070 | 12 | 0.13 |
| IVC$_2$/C$_{18}$ Reverse-phase FPLC | 12,500 | 135 | 0.047 |

*Specific activity is bacteriocin units (BU) divided by the optical density at 280 nm.

After passing through the hydrophobic XAD-16 column, there was a dramatic loss in specific activity with a yield of 3.75% (Table 12, Fraction II). The final purification step resulting in pure ABP118 was reverse-phase chromatography. The active peak, collected as one fraction, eluted at a concentration of 100% isopropanol. When this peak was reapplied to the column, the pure active peak eluted at 31.5% isopropanol. The specific activity of pure ABP118 was 135-fold greater than the culture supernatant and final recovery was 0.047% (Table 12, Fraction IV). Passing through a cation exchange column prior to FPLC decreased specific activity (Table 12, Fraction III) but resulted in better purification. The final protein concentration was estimated to be 130 μg/ml.

Amino Acid Composition and Sequence Analysis

The amino acid composition of pure ABP118 was determined as shown in Table 13.

TABLE 13

Amino acid composition of ABP118

| Amino acid | residues/molecules |
| --- | --- |
| Asp/Asn | 4 |
| Glu/Gln | 2 |
| Ser | 1–2 |
| Gly | 8–10 |
| His | 0–1 |
| Arg | 2 |
| Thr | 2 |
| Ala* | 6 |
| Pro* | 4 |
| Met* | 1 |
| Cys | 1 |
| Ile* | 1 |
| Leu* | 5 |
| Phe* | 2 |
| Lys | 2 |
| Val | 2 |
| Total | 43–47 |

*hydrophobic amino acids

No unusual amino acids were detected. A high proportion of glycine, alanine and leucine was found. No tryptophan or tyrosine residues were present. On Edman degradation, the N-terminus was blocked. As one methionine residue was present, cyanogen bromide cleavage was performed and five amino acid residues were determined at or adjacent to the N-terminus, -Lys-Arg-Gly-Pro-Asn-C (SEQ ID NO: 1). Of the 43–47 amino acids, twenty-one were hydrophobic. The ability to undergo cyanogen bromide cleavage is indicative of the presence of the methionine residue upstream of the lysine residue at the N-terminus.

Mode of Action of ABP 118

ABP118 Adsorbs to Sensitive Cells:

Adsorption of ABP118 was tested over the pH range 4.0–8.0. It was observed that ABP118 bound to the sensitive cells tested (see Table 14) but not to the resistant producer strain L. salivarius UCC 118.

TABLE 14

Adsorption of ABP118 (1600 AU/ml) to sensitive and resistant cells under different pH conditions*

| | ABP118 (AU/ml) unadsorbed | | |
| --- | --- | --- | --- |
| Strain | pH 4.0 | pH 6.0 | pH 8.0 |
| Lactobacillus fermentum KLD (S) | 1000 (40%) | 800 (50%) | 800 (50%) |
| L. salivarius UCC 118 (R) | 1600 (0%) | 1600 (0%) | 1600 (0%) |
| Escherichia coli 1266 (R) | 1600 (0%) | 1600 (0%) | 800 (50%) |
| Bacillus coagulans 1761 (S) | 1000 (40%) | 1000 (40%) | 1000 (40%) |
| Listeria innocua (S) | 1000 (40%) | 1000 (40%) | 1000 (40%) |

*Figures represent unadsorbed ABP118, % adsorption in brackets
S = ABP118-sensitive strain;
R, ABP118-resistant strain ABP118 binding to E. coli 1266 was observed at pH 8.0 but not at the lower pH values tested. After 2 h incubation at 37° C., 40% adsorption of ABP118 to sensitive cells was measured, Total adsorption of 100% was never observed. Less adsorption was found when the experiment was repeated at 4° C. When cells were autoclaved, 40% adsorption was recorded for both sensitive and resistant cells. When cells were treated with protease there was little increase in adsorption to either sensitive or resistant cells.

Figure 6:
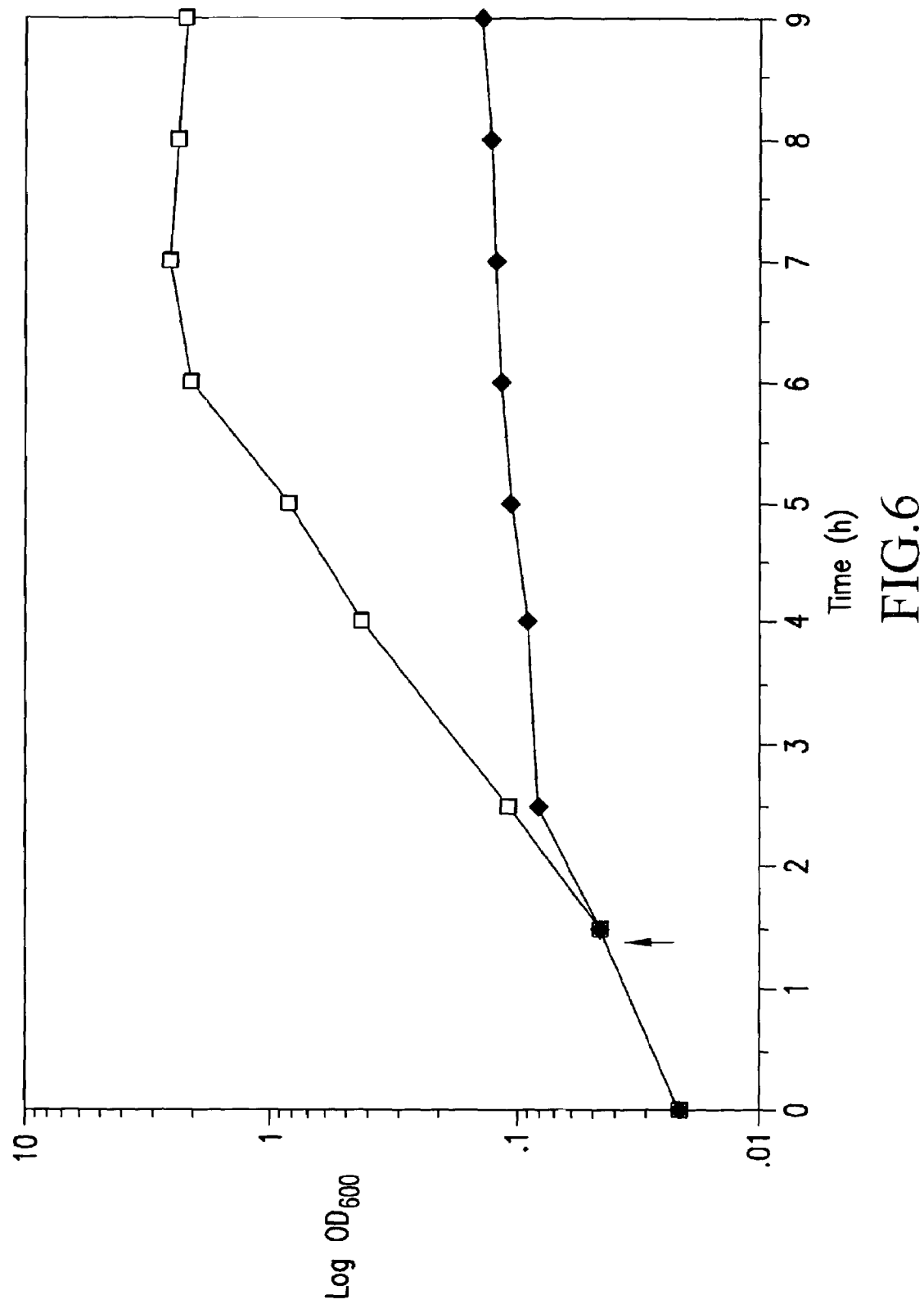
FIG. 6 is a graphic representation of the growth of *Pseudomonas fluorescens* in TSAYE broth with (→) and without (□) addition of ABP118 (5000 AU/ml)
Figure 7:
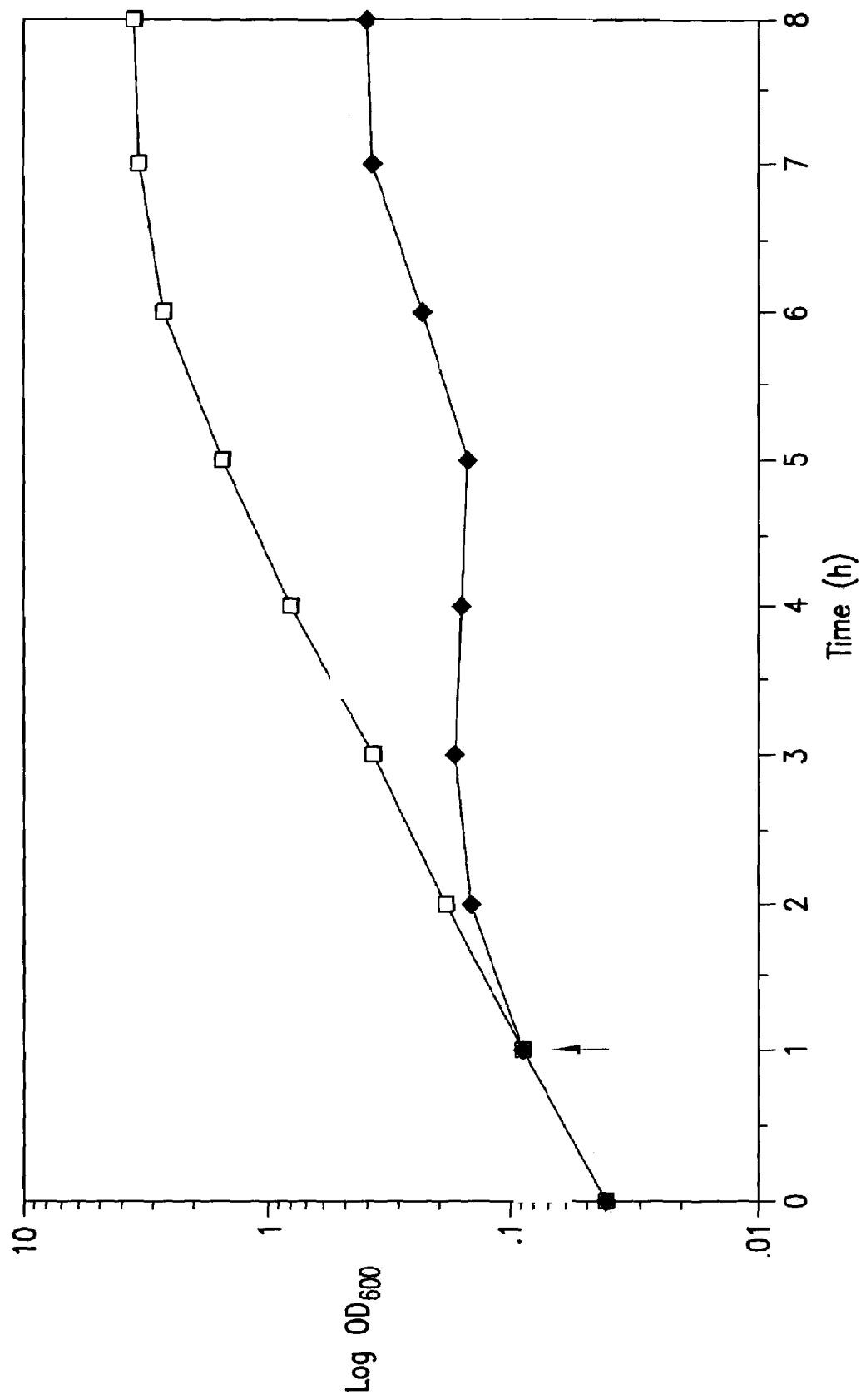
FIG. 7 is a graphic representation of the growth of methicillin resistant *Staphylococcus aureus* 148 (MRSA) in TSAYE broth with (→) and without (□) addition of ABP118 (5000 AU/ml)

ABP118 Possesses Both Bactericidal and Bacteriostatic Activity:

The inhibitor ABP118 is bactericidal in nature. The most impressive example of this was the effect ABP118 had on the growth of *B. coagulans* 1761 during both the log-, and stationary-phase of growth (on both unwashed and washed cells; see FIGS. 5A–5D). The broth cleared during the first couple of hours after addition of ABP118 demonstrating the lytic activity of ABP118. The bactericidal activity towards *Ls. innocua* and *L. fermentum* KLD was more evident in the log-phase of growth than in the stationary-phase. It was noticed that a rapid decline in KLD strain cell viability occurred after incubation of stationary-phase cells for 4 h after the addition of ABP118. The activity of ABP118 (5000 AU/ml) was also tested against a Gram negative *P. fluorescens* strain and a methicillin resistant *S. aureus* strain. After 60–90 min incubation a bacteriostatic effect on the growth of both strains was clearly evident (FIGS. 6 and 7). After 1 h incubation at 30/37° C. the cells were divided in two, ABP118 added to one portion (arrows), and growth was monitored for a further 8–9 h. The line →-→ illustrates the bacteriostatic effect of ABP118.

Figure 8A:
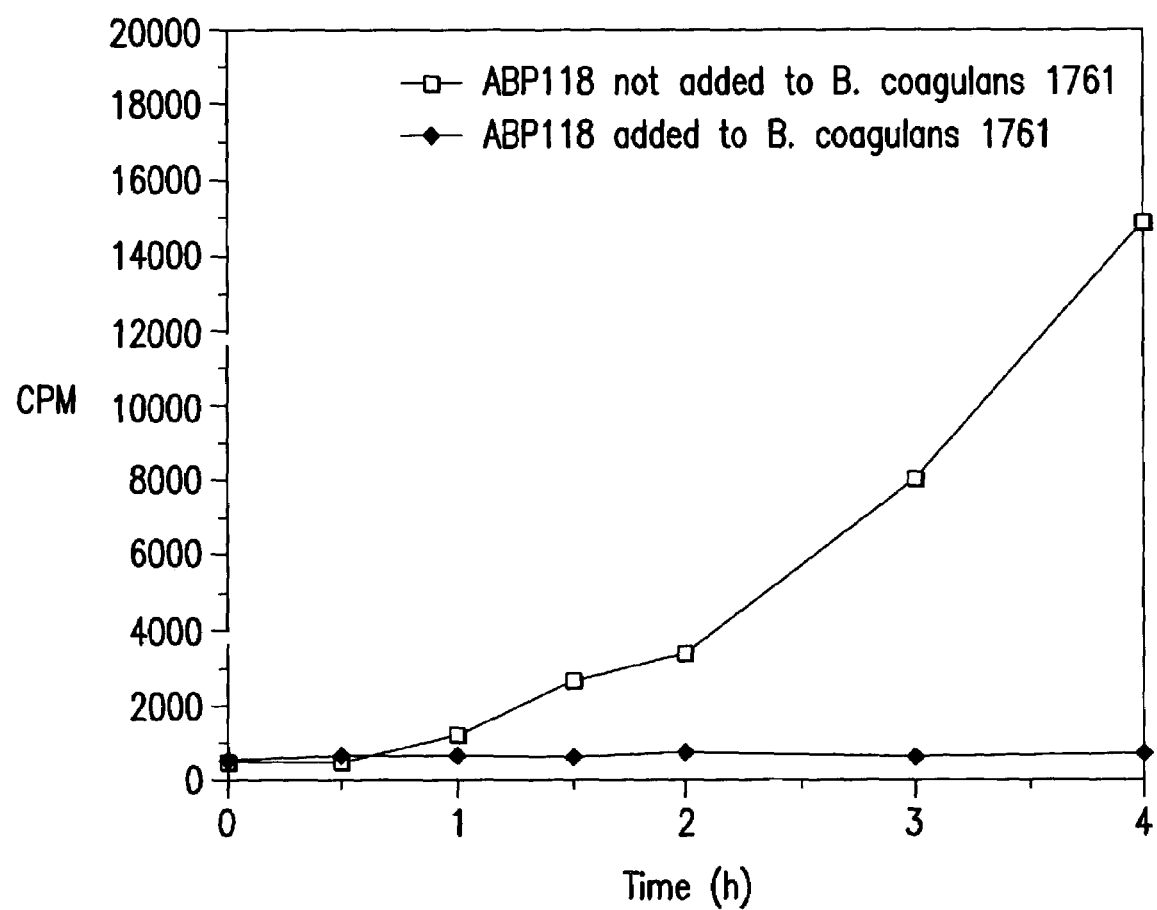
FIG. 8A is a graphic representation of the inhibitory effect of ABP118 on DNA synthesis by *Bacillus coagulans* 1761.
Figure 8B:
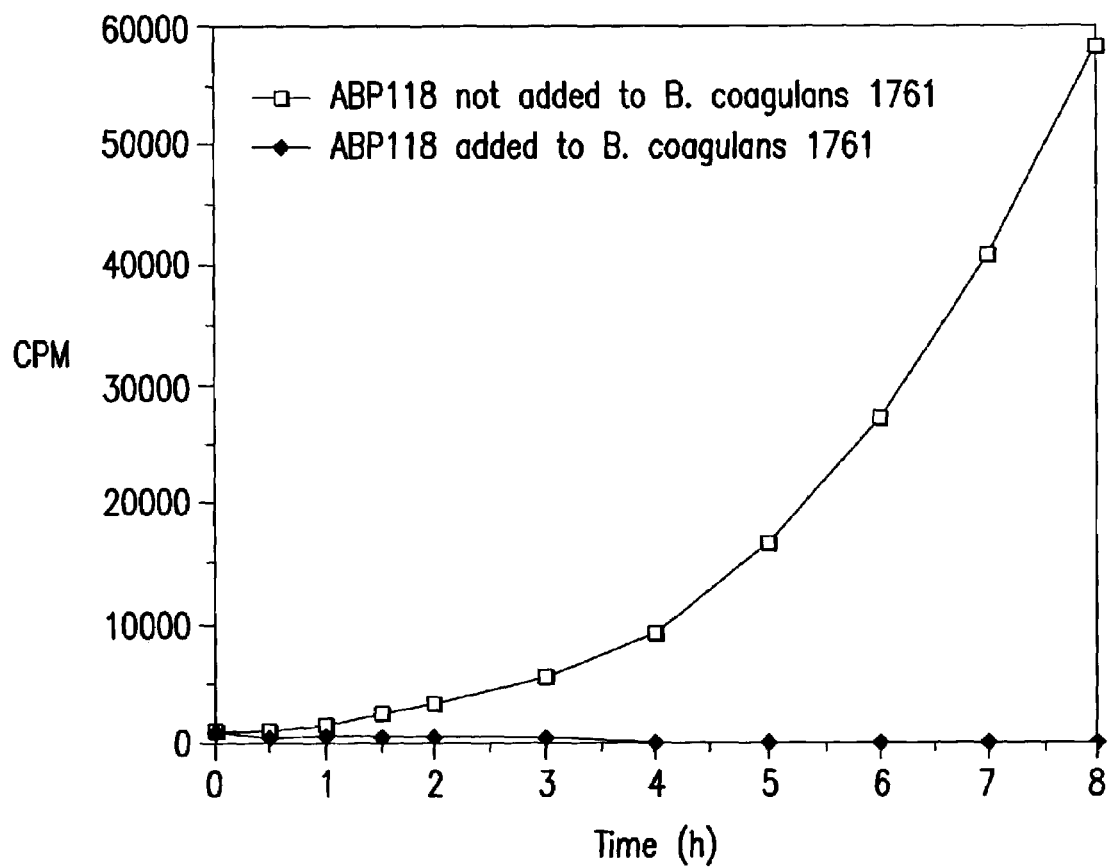
FIG. 8B is a graphic representation of the inhibitory effect of ABP118 on RNA synthesis by *Bacillus coagulans* 1761.

ABP118 Inhibits DNA and RNA Synthesis:

Addition of 5000 AU/ml of ABP118 to log-phase cells did not result in incorporation of either thymidine or uridine indicating that there was inhibition of synthesis of the macromolecules DNA and RNA, respectively. When no bacteriocin was added, cells actively incorporated thymidine and uridine. Inhibition of protein synthesis was not demonstrated due to the low incorporation of radiolabelled amino acid in both the test and control (probably as a result of the high concentration of free amino acids normally present in TSAYE medium). The results are shown in FIG. 8A and FIG. 8B.

EXAMPLE 7

Amino Acid Composition and Sequence Analysis of ABP1

The procedure followed in Example 6 in obtaining the amino acid composition for ABP118 was repeated so as to determine the amino acid composition of pure ABP1. The amino acid composition is shown in Table 15.

TABLE 15

Amino acid composition of ABP1

| Amino acid | residues/molecules |
|---|---|
| Asp/Asn | 5 |
| Glu/Gln | 6 |
| Ser | 5–6 |
| Gly | 8–9 |
| His | 1 |
| Arg | 2–3 |
| Thr | 2 |
| Ala* | 4–5 |
| Pro* | 2 |
| Ile* | 1–2 |
| Leu* | 3 |
| Phe* | 1 |
| Lys | 3 |
| Tyr | 1 |
| Val* | 2–3 |
| Total | 46–52 |

*hydrophobic amino acids

As for ABP118 no unusual amino acids were detected. A high proportion of glycine and alanine was found and a relatively high proportion of leucine. No trytophan was found, however tyrosine and valine were found. Of the 46–52 amino acids, 13–16 were hydrophobic.

EXAMPLE 8

Sequence of ABP118

Total genomic DNA was isolated from UCC118 grown in MRS supplemented with 40 mM DL-threonine by the method of Leenhouts et al. 1991 (J. Bacteriol. 173:4794–4798) and purified by CsCl-ethidium bromide buoyant density gradient centrifugation, with the following modifications. After pelleting and washing the cells in STE buffer, pH 8.0 (6.7% Sucrose, 50 mM Tris/HCl. 1 mM EDTA), the repelleted cells were stored at −20° C. o/n. The cells were lysed using 8 mg/ml lysozyme and 50 U/ml mutanolysin on ice for 1 hour and then incubated at 37° C. for 45 minutes. Before adding SDS solution, 2 mg/ml of proteinase K was added and incubated at 55° C. for 1 hour.

Total genomic DNA for UCC118 was digested with BamHI restriction endonuclease according to the manufacturer's directions (Boehringer Mannheim). Oligonucleotide primers were synthesised on a Beckma Oligo 1000 M DNA synthesizer. A fragment encompassing the putative structural gene of ABP 118 was amplified by the polymerase chain reaction (PCR) using BIOTAQ™ polymerase (Bioline) and was subsequently purified from an agarose gel using the Qiaex II gel extraction kit (Quagen). Cloning was performed in the PGEM-T vector system (Promega) followed by transformation into *E. Coli* JM109 competent cells. Potential pGEM-T recombinants were identified by blue-white screening, using isopropyl-β-D-thiogalactoside and 5-bromo-4-chloro-3-indolyl-β-D-galactoside (X-gal). The presence of inserts was confirmed by PCR using the pGEM-T sequencing primers designed to the known sequences of the T7 and SP6 promoters. These PCR amplified fragments were sequenced by the automated DNA sequencer 373 stretch XL (PE Applied Biosystems) using the Dye terminator cycle sequencing ready reaction kit with Ampli Taq DNA polymerase, FS (Applied Biosystems).

Following cyanogen bromide cleavage and subsequent sequencing, a 30 amino acid sequence from the C-terminal region of ABP118 was obtained including 1 amino acid which could not be identified as indicated below.

```
                                          (SEQ ID NO: 3)
Asn Met Lys Arg Gly Pro Asn ? Val* Gly Asn Phe*

Leu Gly* Gly Leu Phe Ala Gly Ala* Ala* Ala* Gly

Val Pro Leu* Gly Pro-(Ala-Gly-Ile)-Cys.

*indicates probability of more than one amino acid
species at positions 8, 11, 13, 19 20, 21 and 25
? unidentified amino acid
( ) indicates possibility of wrong sequence
```

This sequence was confirmed by PCR with BamHI restricted total DNA using degenerate primers, the forward primers (5'ATGAAACGNGGNCCNAAC3') (SEQ ID NO: 4) being designed to the first six known N-terminal amino acids whereas the reverse primer (5' GGGCCTRNGGNAC-NCC3') (SEQ ID NO: 5) was designed to amino acids 21 to 26, wherein R=purine. An 80 bp. fragment was isolated and subsequently sequenced as follows, (SEQ ID NO: 6)
5'ATGAAACGCGGACCCAACTGTGTAGGTAACTTCTTAGGTGGTCTATTT

GCTGGAGCAGCTGCAGGTGTCCCCCAAGGGCCC3

This DNA sequence was deducted to give the following protein sequence thus confirming the identity of amino acids at positions 7, 8, 11, 13, 19, 20, 21 and 25 in the original sequence.

(SEQ ID NO: 3)
Asn Met Lys Arg Gly Pro Asn Cys Val Gly Asn Phe
Leu Gly Gly Leu Phe Ala Gly Ala Ala Ala Gly Val
Pro Gln Gly Pro Cys.

The DNA sequence showed no homology to known sequences in the data banks.

---

The invention claimed is:

1. A biologically pure culture of a strain of *Lactobacillus salivarius* which is adherent to Caco-2 and HT-29 cells, and is isolated from resected and washed human gastrointestinal tract, wherein said strain of *Lactobacillus salivarius* has the following properties:
   a) binds to human epithelial cells and inhibits a broad range of Gram positive and Gram negative microorganisms;
   b) secretes a product having antimicrobial activity into a cell-free supernatant, wherein said product having antimicrobial activity is produced only by growing cells and wherein said antimicrobial activity is destroyed by proteinase K and pronase E; and
   c) maintains the properties of inhibiting said Gram positive and Gram negative microorganisms, and secreting said product having antimicrobial activity, in the presence of physiological concentrations of human bile and human gastric juice.

2. A biologically pure culture of the strain according to claim 1, wherein the strain has antagonistic activity against bacteria but which does not inhibit closely related *Lactobacillus*.

3. A biologically pure culture of *Lactobacillus salivarius* strain UCC 1 (NCIMB 40830) or a variant thereof having the same antimicrobial and adhesive properties as said UCC 1.

4. A biologically pure culture of *Lactobacillus salivarius* strain UCC 11 8(NCIMB 40829) or a variant thereof having the same antimicrobial and adhesive properties as said UCC 118.

5. A health promoting product containing an isolated or purified strain of *Lactobacillus salivarius* according to any one of claims 1–4 as a probiotic.

6. The biologically pure culture of the strain according to claim 2, wherein said strain has antagonistic activity against a bacterium selected from the group consisting of *Listeria, Staphylococcus, Bacillus, Clostridium, Helicobacter, Pseudomonas, Salmonella, E. coli, Bacteroides* and *Streptococcus pneumonia*.

7. A biologically pure culture of strain of *Lactobacillus salivarius* which is adherent to Caco-2 and HT-29 cells, said strain of *Lactobacillus salivarius* has the following properties:
   a) binds to human epithelial cells and inhibits a broad range of Gram positive and Gram negative microorganisms;
   b) secretes a product having antimicrobial activity into a cell-free supernatant, wherein said product having antimicrobial activity is produced only by growing cells and wherein said antimicrobial activity is destroyed by proteinase K and pronase E;
   c) maintains the properties of inhibiting said Gram positive and Gram negative microorganisms, and secreting said product having antimicrobial activity, in the presence of physiological concentrations of human bile and human gastric juice; and
   d) is isolated from resected and washed human appendix, large intestine or small intestine, and which is adherent thereto.

* * * * *

SEQUENCE LISTING

<160> NUMBER OF SEQ ID NOS: 6

<210> SEQ ID NO 1
<211> LENGTH: 5
<212> TYPE: PRT
<213> ORGANISM: Lactobacillus salivarius

<400> SEQUENCE: 1

Lys Arg Gly Pro Asn
1               5

<210> SEQ ID NO 2
<211> LENGTH: 29
<212> TYPE: PRT
<213> ORGANISM: Lactobacillus salivarius

<400> SEQUENCE: 2

Asn Met Lys Arg Gly Pro Asn Cys Val Gly Asn Phe Leu Gly Gly Leu
1               5                   10                  15

Phe Ala Gly Ala Ala Ala Gly Val Pro Gln Gly Pro Cys
            20                  25

<210> SEQ ID NO 3
<211> LENGTH: 32
<212> TYPE: PRT
<213> ORGANISM: Lactobacillus salivarius
<220> FEATURE:
<221> NAME/KEY: misc_feature
<222> LOCATION: (1)..(32)
<223> OTHER INFORMATION: any Xaa between residues 1-32 is unknown or
      other

<400> SEQUENCE: 3

Asn Met Lys Arg Gly Pro Asn Xaa Val Gly Asn Phe Leu Gly Gly Leu
1               5                   10                  15

Phe Ala Gly Ala Ala Ala Gly Val Pro Leu Gly Pro Ala Gly Ile Cys
            20                  25                  30

<210> SEQ ID NO 4
<211> LENGTH: 18
<212> TYPE: DNA
<213> ORGANISM: Artificial Sequence
<220> FEATURE:
<223> OTHER INFORMATION: primer derived from Lactobacillus salivarius
<220> FEATURE:
<221> NAME/KEY: misc_feature
<222> LOCATION: (1)..(18)
<223> OTHER INFORMATION: any n between residues 1-18 equals a, g, c, t,
      unknown or other

<400> SEQUENCE: 4
atgaaacgng gnccnaac                                                 18

```
<210> SEQ ID NO 5
<211> LENGTH: 16
<212> TYPE: DNA
<213> ORGANISM: Artificial Sequence
<220> FEATURE:
<223> OTHER INFORMATION: primer derived from Lactobacillus salivarius
<220> FEATURE:
<221> NAME/KEY: misc_feature
<222> LOCATION: (1)..(16)
<223> OTHER INFORMATION: any n between residues 1-6 and 8-16 equals
      a, g, c, t, unknown or other
<220> FEATURE:
<221> NAME/KEY: misc_feature
<222> LOCATION: (7)..(7)
<223> OTHER INFORMATION: r at residue 7 equals purine

<400> SEQUENCE: 5
gggcctrngg nacncc                                                    16

<210> SEQ ID NO 6
<211> LENGTH: 80
<212> TYPE: DNA
<213> ORGANISM: Lactobacillus salivarius

<400> SEQUENCE: 6
atgaaacgcg gacccaactg tgtaggtaac ttcttaggtg gtctatttgc tggagcagct    60
gcaggtgtcc cccagggccc                                                80
```